US012745937B2

(12) United States Patent
Rahman et al.

(10) Patent No.: US 12,745,937 B2
(45) Date of Patent: Sep. 29, 2026

(54) SYSTEMS AND METHODS TO DETECT AND CHARACTERIZE STRESS USING PHYSIOLOGICAL SENSORS

(71) Applicant: Samsung Electronics Co., Ltd., Suwon-si (KR)

(72) Inventors: Md Mahbubur Rahman, San Jose, CA (US); Viswam Nathan, Clovis, CA (US); Li Zhu, Saratoga, CA (US); Tousif Ahmed, San Jose, CA (US); Jungmok Bae, Menlo Park, CA (US); Jilong Kuang, San Jose, CA (US); Jeong Woo Kim, Danville, CA (US); Jun Gao, Menlo Park, CA (US)

(73) Assignee: Samsung Electronics Co., Ltd., Suwon-si (KR)

( * ) Notice: Subject to any disclaimer, the term of this patent is extended or adjusted under 35 U.S.C. 154(b) by 637 days.

(21) Appl. No.: 18/156,292

(22) Filed: Jan. 18, 2023

(65) Prior Publication Data

US 2023/0233123 A1 Jul. 27, 2023

Related U.S. Application Data

(60) Provisional application No. 63/302,524, filed on Jan. 24, 2022.

(51) Int. Cl.
*A61B 5/16* (2006.01)
*A61B 5/00* (2006.01)

(52) U.S. Cl.
CPC .............. *A61B 5/165* (2013.01); *A61B 5/486* (2013.01); *A61B 5/6802* (2013.01); *A61B 5/7246* (2013.01); *A61B 5/7267* (2013.01)

(58) Field of Classification Search
CPC ....... A61B 5/165; A61B 5/486; A61B 5/6802; A61B 5/7246; A61B 5/7267
See application file for complete search history.

(56) References Cited

U.S. PATENT DOCUMENTS 10,468,140 B2 11/2019 Wright et al.
11,311,198 B2 4/2022 Jayaraman et al.
(Continued)

FOREIGN PATENT DOCUMENTS

CN 107852540 A * 3/2018 ............. H04R 1/105
EP 3419519 B1 7/2020
(Continued)

OTHER PUBLICATIONS

Supplementary European Search Report dated Nov. 4, 2024, in connection with European Patent Application No. 23743520.1, 10 pages.

(Continued)

*Primary Examiner* — Amanda L Steinberg
*Assistant Examiner* — Laura Hodge

(57) ABSTRACT

A method includes receiving multimodal data collected using at least one wearable device during an assessment window. The method also includes extracting biomarker features from the multimodal data, based on changes in the extracted biomarker features. The method also includes detecting that a stress event occurred during the assessment window. The method also includes accessing a plurality of templates of patterns in biomarker features, wherein a first subset of the templates is associated with unhealthy response to stress and a second subset of the templates is associated with healthy response to stress. The method also includes determining whether the stress event corresponds to a healthy response or an unhealthy response based on similarities between a pattern in the extracted biomarker features and the plurality of templates. The method also includes responsive to the stress event corresponding to an unhealthy response, providing a stress management recommendation.

20 Claims, 21 Drawing Sheets

(56) References Cited

U.S. PATENT DOCUMENTS

| | | | | |
|---|---|---|---|---|
| 11,432,769 | B2 | 9/2022 | Gottesman | |
| 2012/0289793 | A1 | 11/2012 | Jain et al. | |
| 2013/0041715 | A1 | 2/2013 | Tomoeda | |
| 2014/0046144 | A1 | 2/2014 | Jayaraman et al. | |
| 2014/0121540 | A1 | 5/2014 | Raskin | |
| 2017/0071551 | A1 | 3/2017 | Jain et al. | |
| 2017/0119297 | A1 | 5/2017 | Flax et al. | |
| 2017/0156657 | A1 | 6/2017 | Flax et al. | |
| 2018/0078188 | A1 | 3/2018 | Kaneko et al. | |
| 2018/0235483 | A1 * | 8/2018 | Mouradian | G06F 1/163 |
| 2019/0133537 | A1 * | 5/2019 | Ghose | A61B 5/7278 |
| 2019/0231221 | A1 * | 8/2019 | Shin | A61B 5/7278 |
| 2019/0365263 | A1 * | 12/2019 | Raj | A61B 5/0024 |
| 2021/0052198 | A1 * | 2/2021 | Parvaneh | A61B 5/1117 |
| 2021/0059539 | A1 | 3/2021 | Parchani et al. | |
| 2022/0176065 | A1 | 6/2022 | Youngblood et al. | |
| 2022/0249022 | A1 | 8/2022 | Toth et al. | |

FOREIGN PATENT DOCUMENTS

| | | | | | |
|---|---|---|---|---|---|
| KR | 10-2011-0008434 | A | | 1/2011 | |
| KR | 20180031610 | A | * | 3/2018 | A61B 5/0488 |
| KR | 10-2019-0050618 | A | | 5/2019 | |
| KR | 20220133081 | A | | 10/2022 | |
| WO | 2022212052 | A1 | | 10/2022 | |

OTHER PUBLICATIONS

Rahman, et al., "Detecting Physiological Responses Using Multimodal Earbud Sensors", 2022 44th Annual International Conference of the IEEE Engineering in Medicine & Biology Society (EMBC), Date of Conference: Jul. 11-15, 2022, Sep. 8, 2022, 5 pages.

Sano, et al., "Stress Recognition Using Wearable Sensors and Mobile Phones," 2013 Humaine Association Conference on Affective Computing and Intelligent Interaction, IEEE Computer Society, Sep. 2, 2013, 6 pages.

Mishra, et al., "Evaluating the Reproducibility of Physiological Stress Detection Models," Proc. ACM Interact. Mob. Wearable Ubiquitous Technol., vol. 4, No. 4, Article 147, Dec. 2020, 29 pages.

Hovsepian et al., "cStress: Towards a Gold Standard for Continuous Stress Assessment in the Mobile Environment," Proc. ACM Int. Conf. Ubiquitous Comput., Nov. 3, 2015, 33 pages.

Gjoreski, M., et al., "Continuous Stress Detection Using a Wrist Device—In Laboratory and Real Life", UbiComp '16: Proceedings of the 2016 ACM International Joint Conference on Pervasive and Ubiquitous Computing: Adjunct, Sep. 12, 2016, 9 pages.

International Search Report and Written Opinion of the International Searching Authority dated May 1, 2023, in connection with International Application No. PCT/KR2023/000993, 8 pages.

* cited by examiner

| | | $S_i$ | |
|---|---|---|---|
| $S_{i-1}$ | $Z_{i-1}$ | 1 | 0 |
| 1 | 1 | 1 | 0 |
| 1 | 0 | α | 1−α |
| 1 | 0 | β | 1−β |
| 1 | 0 | 0 | 1 |

SYSTEMS AND METHODS TO DETECT AND CHARACTERIZE STRESS USING PHYSIOLOGICAL SENSORS

CROSS-REFERENCE TO RELATED APPLICATION AND PRIORITY CLAIM

This application claims priority under 35 U.S.C. § 119(e) to U.S. Provisional Patent Application No. 63/302,524 filed on Jan. 24, 2022. This provisional application is hereby incorporated by reference in its entirety.

TECHNICAL FIELD

This disclosure relates generally to machine learning systems. More specifically, this disclosure relates to systems and methods to detect and characterize stress using physiological sensors.

BACKGROUND

Physiologically, "stress" may be viewed as the balance between sympathetic and parasympathetic nervous system activities. The sympathetic system activates the person to face the stressful situation, and the parasympathetic system helps recover from the arousal and maintain a physiological balance of the body. Various stressors in daily life can trigger physiological responses that may either be detrimental to mental and physical well-being or be useful to increase focus and productivity. However, repeated exposure to stress can accumulate and is linked to cardiovascular diseases and essential hypertension. Continuous stress exposure negatively impacts mental and physical well-being.

Physiological stress responses are multi-faceted, known to affect breathing rate, depth, and symmetry, and to cause a decrease in peripheral skin temperature while increasing core temperature. That is, physiological arousal due to stress affects heart-beat frequency and blood volume pulse, and changes the breathing pattern and peripheral temperature, among several other bodily responses. Continuous physiological stress measurement combined with stress categorization (i.e., as detrimental or favorable) can be useful for developing better stress management technologies.

Traditionally, stress is detected by assessing cortisol in body fluid (such as saliva) or via self-reporting by users. Alternatively, signals such as electrocardiogram (ECG), respiration, and skin conductance responses may be captured using wearables for stress monitoring and management. However, stress affects different organs differently and usually multiple devices are placed in different parts of the body to capture the multi-modal stress response. Moreover, this type of setup is expensive and inconvenient for daily use. Existing stress detection models cannot distinguish the beneficial types of stress and harmful types of stress, since sympathetic nervous system responses (such as heart rate, galvanic skin response (GSR)) can be similar in both cases. Furthermore, existing algorithms cannot detect the stressor type—whether the stress is cognitive, physical, or social—and hence fail to contextualize the stress relieving intervention accordingly.

SUMMARY

This disclosure relates to systems and methods to detect and characterize stress using physiological sensors. This disclosure provides for stress detection and characterization using multimodal physiological stress response data collected during an assessment window using at least one wearable device, such as earbuds. Based on changes in biomarker features extracted from the multimodal data, the occurrence of a stress event during the assessment window is detected. A plurality of templates of patterns in biomarker features includes a first subset of the templates associated with unhealthy response(s) to stress and a second subset of the templates associated with healthy response(s) to stress. Correspondence of the stress event to a healthy response or an unhealthy response is determined based on similarities between a pattern in the extracted biomarker features and the plurality of templates. When the stress event is determined to correspond to an unhealthy response, a stress management recommendation is provided.

In a first embodiment, a method includes receiving multimodal data collected using at least one wearable device during an assessment window. The method also includes extracting biomarker features from the multimodal data. The method also includes, based on changes in the extracted biomarker features, detecting that a stress event occurred during the assessment window. The method also includes accessing a plurality of templates of patterns in biomarker features, a first subset of the templates associated with an unhealthy response to stress and a second subset of the templates associated with a healthy response to stress. The method also includes determining whether the stress event corresponds to a healthy response or an unhealthy response based on similarities between a pattern in the extracted biomarker features and the plurality of templates. The method also includes, responsive to the stress event corresponding to an unhealthy response, providing a stress management recommendation.

In a second embodiment, an apparatus includes at least one processing device configured to receive multimodal data collected using at least one wearable device during an assessment window. The at least one processing device is also configured to extract biomarker features from the multimodal data. The at least one processing device is also configured to, based on changes in the extracted biomarker features, detect that a stress event occurred during the assessment window. The at least one processing device is also configured to access a plurality of templates of patterns in biomarker features, a first subset of the templates associated with unhealthy response to stress and a second subset of the templates associated with healthy response to stress. The at least one processing device is also configured to determine whether the stress event corresponds to a healthy response or an unhealthy response based on similarities between a pattern in the extracted biomarker features and the plurality of templates. The at least one processing device is also configured to, responsive to the stress event corresponding to an unhealthy response, provide a stress management recommendation.

In a third embodiment, a non-transitory computer readable medium contains instructions that, when executed, cause at least one processor of an electronic device to receive multimodal data collected using at least one wearable device during an assessment window. The non-transitory computer readable medium also contains instructions that when executed cause the at least one processor to extract biomarker features from the multimodal data. The non-transitory computer readable medium also contains instructions that when executed cause the at least one processor to, based on changes in the extracted biomarker features, detect that a stress event occurred during the assessment window. The non-transitory computer readable medium also contains instructions that when executed cause the at least one processor to access a plurality of templates of patterns in biomarker features, wherein a first subset of the templates is associated with unhealthy response to stress and a second subset of the templates is associated with healthy response to stress. The non-transitory computer readable medium also contains instructions that when executed cause the at least one processor to determine whether the stress event corresponds to a healthy response or an unhealthy response based on similarities between a pattern in the extracted biomarker features and the plurality of templates. The non-transitory computer readable medium also contains instructions that when executed cause the at least one processor to, responsive to the stress event corresponding to an unhealthy response, provide a stress management recommendation.

In any of the foregoing embodiments, the multimodal data may include one or more of photoplethysmography (PPG) data, inertial measurement unit (IMU) data, electrocardiogram data, and body temperature data.

In any of the foregoing embodiments, the at least one wearable device may be one of earbuds, a watch, or a phone.

In any of the foregoing embodiments, the biomarker features may include one or more of: a heart rate, a time domain heart rate variability, a frequency domain heart rate variability, a non-linear heart rate variability, a breathing rate, an inhalation to exhalation ratio, a depth of breathing, a cardiac output, a stroke volume, a pulse transit time, or a pre-ejection period.

In any of the foregoing embodiments, the templates may be associated with one or more of an anticipatory reaction, a lack of recovery, a lack of habituation, and repeated exposure.

In any of the foregoing embodiments, the determination of whether the stress event is a healthy response or an unhealthy response further may include, for each of the plurality of templates, determining a similarity score between the pattern in the extracted biomarker features and the respective template, and providing similarity scores and one or more response features associated with the extracted biomarker features as input to a machine learning model, where the machine learning model is trained to predict whether the stress event is a healthy response or an unhealthy response based on a probability distribution.

In any of the foregoing embodiments, the response features may include one or more of a level of changes from a baseline, elevation patterns, recovery patterns, an elevation duration, and a total stress event duration.

In a fourth embodiment, a method includes obtaining multi-modal physiological stress response data. The method also includes detecting significant stress arousal from the multi-modal physiological stress response data. The method also includes determining an arousal and recovery pattern for a detected significant stress arousal, including an elevation pattern, a recovery pattern, an arousal duration, and a total response cycle duration. The method also includes using a machine learning model trained to characterize stress based on selected multi-modal biomarker features to infer that the determined arousal and recovery pattern is healthy or unhealthy, and to tag a type for stress associated with the determined arousal and recovery pattern as one of a physical type, a social type, or a cognitive type.

Other technical features may be readily apparent to one skilled in the art from the following figures, descriptions, and claims.

Before undertaking the DETAILED DESCRIPTION below, it may be advantageous to set forth definitions of certain words and phrases used throughout this patent document. The terms "transmit," "receive," and "communicate," as well as derivatives thereof, encompass both direct and indirect communication. The terms "include" and "comprise," as well as derivatives thereof, mean inclusion without limitation. The term "or" is inclusive, meaning and/or. The phrase "associated with," as well as derivatives thereof, means to include, be included within, interconnect with, contain, be contained within, connect to or with, couple to or with, be communicable with, cooperate with, interleave, juxtapose, be proximate to, be bound to or with, have, have a property of, have a relationship to or with, or the like.

Moreover, various functions described below can be implemented or supported by one or more computer programs, each of which is formed from computer readable program code and embodied in a computer readable medium. The terms "application" and "program" refer to one or more computer programs, software components, sets of instructions, procedures, functions, objects, classes, instances, related data, or a portion thereof adapted for implementation in a suitable computer readable program code. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc (CD), a digital video disc (DVD), or any other type of memory. A "non-transitory" computer readable medium excludes wired, wireless, optical, or other communication links that transport transitory electrical or other signals. A non-transitory computer readable medium includes media where data can be permanently stored and media where data can be stored and later overwritten, such as a rewritable optical disc or an erasable memory device.

As used here, terms and phrases such as "have," "may have," "include," or "may include" a feature (like a number, function, operation, or component such as a part) indicate the existence of the feature and do not exclude the existence of other features. Also, as used here, the phrases "A or B," "at least one of A and/or B," or "one or more of A and/or B" may include all possible combinations of A and B. For example, "A or B," "at least one of A and B," and "at least one of A or B" may indicate all of (1) including at least one A, (2) including at least one B, or (3) including at least one A and at least one B. Further, as used here, the terms "first" and "second" may modify various components regardless of importance and do not limit the components. These terms are only used to distinguish one component from another. For example, a first user device and a second user device may indicate different user devices from each other, regardless of the order or importance of the devices. A first component may be denoted a second component and vice versa without departing from the scope of this disclosure.

It will be understood that, when an element (such as a first element) is referred to as being (operatively or communicatively) "coupled with/to" or "connected with/to" another element (such as a second element), it can be coupled or connected with/to the other element directly or via a third element. In contrast, it will be understood that, when an element (such as a first element) is referred to as being "directly coupled with/to" or "directly connected with/to" another element (such as a second element), no other element (such as a third element) intervenes between the element and the other element.

As used here, the phrase "configured (or set) to" may be interchangeably used with the phrases "suitable for," "having the capacity to," "designed to," "adapted to," "made to," or "capable of" depending on the circumstances. The phrase "configured (or set) to" does not essentially mean "specifically designed in hardware to." Rather, the phrase "configured to" may mean that a device can perform an operation together with another device or parts. For example, the phrase "processor configured (or set) to perform A, B, and C" may mean a generic-purpose processor (such as a CPU or application processor) that may perform the operations by executing one or more software programs stored in a memory device or a dedicated processor (such as an embedded processor) for performing the operations.

The terms and phrases as used here are provided merely to describe some embodiments of this disclosure but not to limit the scope of other embodiments of this disclosure. It is to be understood that the singular forms "a," "an," and "the" include plural references unless the context clearly dictates otherwise. All terms and phrases, including technical and scientific terms and phrases, used here have the same meanings as commonly understood by one of ordinary skill in the art to which the embodiments of this disclosure belong. It will be further understood that terms and phrases, such as those defined in commonly-used dictionaries, should be interpreted as having a meaning that is consistent with their meaning in the context of the relevant art and will not be interpreted in an idealized or overly formal sense unless expressly so defined here. In some cases, the terms and phrases defined here may be interpreted to exclude embodiments of this disclosure.

Examples of an "electronic device" according to embodiments of this disclosure may include at least one of a smartphone, a tablet personal computer (PC), a mobile phone, a video phone, an e-book reader, a desktop PC, a laptop computer, a netbook computer, a workstation, a personal digital assistant (PDA), a portable multimedia player (PMP), an MP3 player, a mobile medical device, a camera, or a wearable device (such as smart glasses, a head-mounted device (HMD), earbuds, electronic clothes, an electronic bracelet, an electronic necklace, an electronic accessory, an electronic tattoo, a smart mirror, or a smart watch). Other examples of an electronic device include a smart home appliance. Examples of the smart home appliance may include at least one of a television, a digital video disc (DVD) player, an audio player, a refrigerator, an air conditioner, a cleaner, an oven, a microwave oven, a washer, a drier, an air cleaner, a set-top box, a home automation control panel, a security control panel, a TV box (such as SAMSUNG HOMESYNC, APPLETV, or GOOGLE TV), a smart speaker or speaker with an integrated digital assistant (such as SAMSUNG GALAXY HOME, APPLE HOMEPOD, or AMAZON ECHO), a gaming console (such as an XBOX, PLAYSTATION, or NINTENDO), an electronic dictionary, an electronic key, a camcorder, or an electronic picture frame. Still other examples of an electronic device include at least one of various medical devices (such as diverse portable medical measuring devices (like a blood sugar measuring device, a heartbeat measuring device, or a body temperature measuring device), a magnetic resource angiography (MRA) device, a magnetic resource imaging (MRI) device, a computed tomography (CT) device, an imaging device, or an ultrasonic device), a navigation device, a global positioning system (GPS) receiver, an event data recorder (EDR), a flight data recorder (FDR), an automotive infotainment device, a sailing electronic device (such as a sailing navigation device or a gyro compass), avionics, security devices, vehicular head units, industrial or home robots, automatic teller machines (ATMs), point of sales (POS) devices, or Internet of Things (IoT) devices (such as a bulb, various sensors, electric or gas meter, sprinkler, fire alarm, thermostat, street light, toaster, fitness equipment, hot water tank, heater, or boiler). Other examples of an electronic device include at least one part of a piece of furniture or building/structure, an electronic board, an electronic signature receiving device, a projector, or various measurement devices (such as devices for measuring water, electricity, gas, or electromagnetic waves). Note that, according to various embodiments of this disclosure, an electronic device may be one or a combination of the above-listed devices. According to some embodiments of this disclosure, the electronic device may be a flexible electronic device. The electronic device disclosed here is not limited to the above-listed devices and may include new electronic devices depending on the development of technology.

In the following description, electronic devices are described with reference to the accompanying drawings, according to various embodiments of this disclosure. As used here, the term "user" may denote a human or another device (such as an artificial intelligent electronic device) using the electronic device.

Definitions for other certain words and phrases may be provided throughout this patent document. Those of ordinary skill in the art should understand that in many if not most instances, such definitions apply to prior as well as future uses of such defined words and phrases.

None of the description in this application should be read as implying that any particular element, step, or function is an essential element that must be included in the claim scope. The scope of patented subject matter is defined only by the claims. Moreover, none of the claims is intended to invoke 35 U.S.C. § 112(f) unless the exact words "means for" are followed by a participle. Use of any other term, including without limitation "mechanism," "module," "device," "unit," "component," "element," "member," "apparatus," "machine," "system," "processor," or "controller," within a claim is understood by the Applicant to refer to structures known to those skilled in the relevant art and is not intended to invoke 35 U.S.C. § 112(f).

BRIEF DESCRIPTION OF THE DRAWINGS

For a more complete understanding of this disclosure and its advantages, reference is now made to the following description taken in conjunction with the accompanying drawings, in which like reference numerals represent like parts.

DETAILED DESCRIPTION

Figure 1:
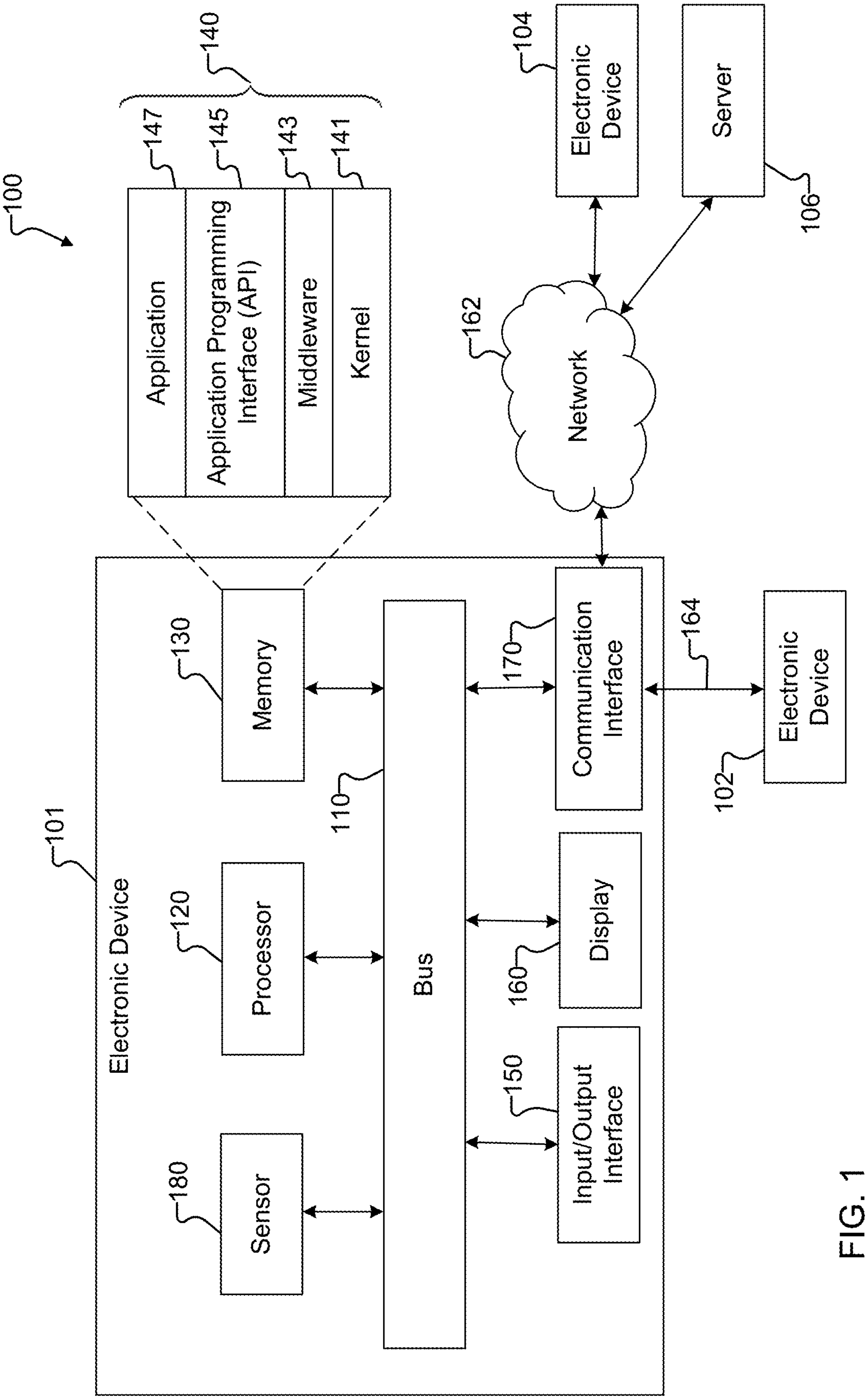
FIG. 1 illustrates an example network configuration including an electronic device in accordance with this disclosure.

FIGS. 1 through 27, discussed below, and the various embodiments of this disclosure are described with reference to the accompanying drawings. However, it should be appreciated that this disclosure is not limited to these embodiments, and all changes and/or equivalents or replacements thereto also belong to the scope of this disclosure. The same or similar reference denotations may be used to refer to the same or similar elements throughout the specification and the drawings.

As noted above, physiologically, "stress" may be viewed as the balance between sympathetic and parasympathetic nervous system activities. The sympathetic system activates the person to face the stressful situation, and the parasympathetic system helps recover from the arousal and maintain physiological balance of the body. Various stressors in daily life can trigger physiological responses that may either be detrimental to mental and physical well-being or be useful to increase focus and productivity. However, repeated exposure to stress can accumulate and is linked to cardiovascular diseases and essential hypertension. Continuous stress exposure negatively impacts mental and physical well-being.

Physiological stress responses are multi-faceted, known to affect breathing rate, depth, and symmetry, and to cause a decrease in peripheral skin temperature while increasing core temperature. That is, physiological arousal due to stress affects heart-beat frequency and blood volume pulse, and changes the breathing pattern and peripheral temperature, among several other bodily responses. Continuous physiological stress measurement combined with stress categorization (i.e., as detrimental or favorable) can be useful for developing better stress management technologies. Multimodal approaches appear to have good stress classification accuracy.

Traditionally, stress is detected by assessing cortisol in body fluid (such as saliva) or via self-reporting by users. Feasibility of capturing signals such as electrocardiogram (ECG), respiration, and skin conductance responses using wearables has shown promise in stress monitoring and management. Stress affects different organs differently and usually multiple devices are placed in different parts of the body to capture the multi-modal stress response. This type of setup is expensive and inconvenient for daily use. Existing stress detection models cannot distinguish the good and bad, since sympathetic nervous system response (such as heart rate, galvanic skin response (GSR)) can be similar in both cases. Furthermore, existing algorithms cannot detect the stressor type—whether the stress is cognitive, physical, or social—and hence fail to contextualize the stress relieving intervention accordingly.

This disclosure provides multi-modal sensors in the same wearable device(s) (earbuds, watch, eye-glasses) that are used to detect stress. The multi-modal sensors may include photoplethysmography (PPG) sensor(s), an inertial measurement (IMU), and body temperature sensor(s). The IMU sensor in the wearable (earbud, is utilized to determine three components:

- lung motion is captured to estimate breathing biomarkers (breathing rate, depth, and inhale-exhale ratio);
- subtle ballistic motion due to heart pumping the blood is captured to estimate heart rate, heart rate variability, and hemodynamic biomarkers such as cardiac output (CO), stroke volume (SV), pulse transit time (PTT) (in conjunction with the PPG sensor(s)); and
- motion artifact detection is facilitated, where the motion artifact(s) are due to head or body motion that interferes with the biomarker estimation, to determine the quality of the measured data.

By capturing multi-modal stress responses, this disclosure characterizes the stress arousal as good (healthy) or bad (unhealthy) stress, while also detecting the type of stress as social, cognitive, or physical stress (or the like) for just-in-time adaptive stress interventions. Such interventions can be useful for precision stress management. The disclosure provides:

- detecting significant stress arousal passively in a time-series data;
- extracting hemodynamic and breathing biomarkers using novel approaches utilizing IMU and PPG data;
- detecting significant arousal based on arousal intensity and arousal duration;
- distinguishing good and bad stress by estimating multi-modal physiological biomarkers;

identifying arousal and recovery patterns for healthy and unhealthy response detection;

deriving a similarity metric for identifying healthy and unhealthy stress response;

detecting the type (social/cognitive/physical) of the arousal from physiological stress responses; and detecting subtle difference in stress responses on weakly labeled data using machine learning/AI on multi-modal biomarkers.

FIG. 1 illustrates an example network configuration 100 including an electronic device in accordance with this disclosure. The embodiment of the network configuration 100 shown in FIG. 1 is for illustration only. Other embodiments of the network configuration 100 could be used without departing from the scope of this disclosure.

According to embodiments of this disclosure, an electronic device 101 is included in the network configuration 100. The electronic device 101 can include at least one of a bus 110, a processor 120, a memory 130, an input/output (I/O) interface 150, a display 160, a communication interface 170, or a sensor 180. In some embodiments, the electronic device 101 may exclude at least one of these components or may add at least one other component. The bus 110 includes a circuit for connecting the components 120-180 with one another and for transferring communications (such as control messages and/or data) between the components.

The processor 120 includes one or more processing devices, such as one or more microprocessors, microcontrollers, digital signal processors (DSPs), application specific integrated circuits (ASICs), or field programmable gate arrays (FPGAs). In some embodiments, the processor 120 includes one or more of a central processing unit (CPU), an application processor (AP), a communication processor (CP), or a graphics processor unit (GPU). The processor 120 is able to perform control on at least one of the other components of the electronic device 101 and/or perform an operation or data processing relating to communication or other functions. As described below, the processor 120 may be used to detect and characterize stress using physiological sensors.

The memory 130 can include a volatile and/or non-volatile memory. For example, the memory 130 can store commands or data related to at least one other component of the electronic device 101. According to embodiments of this disclosure, the memory 130 can store software and/or a program 140. The program 140 includes, for example, a kernel 141, middleware 143, an application programming interface (API) 145, and/or an application program (or "application") 147. At least a portion of the kernel 141, middleware 143, or API 145 may be denoted an operating system (OS).

The kernel 141 can control or manage system resources (such as the bus 110, processor 120, or memory 130) used to perform operations or functions implemented in other programs (such as the middleware 143, API 145, or application 147). The kernel 141 provides an interface that allows the middleware 143, the API 145, or the application 147 to access the individual components of the electronic device 101 to control or manage the system resources. The application 147 includes one or more applications for detecting and characterizing stress using physiological sensors. These functions can be performed by a single application or by multiple applications that each carries out one or more of these functions. The middleware 143 can function as a relay to allow the API 145 or the application 147 to communicate data with the kernel 141, for instance. A plurality of applications 147 can be provided. The middleware 143 is able to control work requests received from the applications 147, such as by allocating the priority of using the system resources of the electronic device 101 (like the bus 110, the processor 120, or the memory 130) to at least one of the plurality of applications 147. The API 145 is an interface allowing the application 147 to control functions provided from the kernel 141 or the middleware 143. For example, the API 145 includes at least one interface or function (such as a command) for filing control, window control, image processing, or text control.

The I/O interface 150 serves as an interface that can, for example, transfer commands or data input from a user or other external devices to other component(s) of the electronic device 101. The I/O interface 150 can also output commands or data received from other component(s) of the electronic device 101 to the user or the other external device.

The display 160 includes, for example, a liquid crystal display (LCD), a light emitting diode (LED) display, an organic light emitting diode (OLED) display, a quantum-dot light emitting diode (QLED) display, a microelectromechanical systems (MEMS) display, or an electronic paper display. The display 160 can also be a depth-aware display, such as a multi-focal display. The display 160 is able to display, for example, various contents (such as text, images, videos, icons, or symbols) to the user. The display 160 can include a touchscreen and may receive, for example, a touch, gesture, proximity, or hovering input using an electronic pen or a body portion of the user.

The communication interface 170, for example, is able to set up communication between the electronic device 101 and an external electronic device (such as a first electronic device 102, a second electronic device 104, or a server 106). For example, the communication interface 170 can be connected with a network 162 or 164 through wireless or wired communication to communicate with the external electronic device. The communication interface 170 can be a wired or wireless transceiver or any other component for transmitting and receiving signals, such as images.

The electronic device 101 further includes one or more sensors 180 that can meter a physical quantity or detect an activation state of the electronic device 101 and convert metered or detected information into an electrical signal. For example, one or more sensors 180 may include one or more cameras or other imaging sensors, which may be used to capture images of scenes. The sensor(s) 180 can also include one or more buttons for touch input, one or more microphones, a gesture sensor, a gyroscope or gyro sensor, an air pressure sensor, a magnetic sensor or magnetometer, an acceleration sensor or accelerometer, a grip sensor, a proximity sensor, a color sensor (such as an RGB sensor), a bio-physical sensor, a temperature sensor, a humidity sensor, an illumination sensor, an ultraviolet (UV) sensor, an electromyography (EMG) sensor, an electroencephalogram (EEG) sensor, an electrocardiogram (ECG) sensor, an infrared (IR) sensor, an ultrasound sensor, an iris sensor, or a fingerprint sensor. The sensor(s) 180 can further include an inertial measurement unit, which can include one or more accelerometers, gyroscopes, and other components. In addition, the sensor(s) 180 can include a control circuit for controlling at least one of the sensors included here. Any of these sensor(s) 180 can be located within the electronic device 101.

The first external electronic device 102 or the second external electronic device 104 can be a wearable device or an electronic device-mountable wearable device (such as an HMD). When the electronic device 101 is mounted in the electronic device 102 (such as the HMD), the electronic device 101 can communicate with the electronic device 102 through the communication interface 170. The electronic device 101 can be directly connected with the electronic device 102 to communicate with the electronic device 102 without involving with a separate network. The electronic device 101 can also be an augmented reality wearable device, such as eyeglasses, which includes one or more cameras.

The wireless communication is able to use at least one of, for example, long term evolution (LTE), long term evolution-advanced (LTE-A), 5th Generation (5G) wireless system, millimeter-wave or 60 GHz wireless communication, Wireless USB, code division multiple access (CDMA), wideband code division multiple access (WCDMA), universal mobile telecommunication system (UMTS), wireless broadband (WiBro), or global system for mobile communication (GSM), as a cellular communication protocol. The wired connection can include, for example, at least one of a universal serial bus (USB), high definition multimedia interface (HDMI), recommended standard 232 (RS-232), or plain old telephone service (POTS). The network 162 includes at least one communication network, such as a computer network (like a local area network (LAN) or wide area network (WAN)), Internet, or a telephone network.

The first and second external electronic devices 102 and 104 and server 106 each can be a device of the same or a different type from the electronic device 101. According to certain embodiments of this disclosure, the server 106 includes a group of one or more servers. Also, according to certain embodiments of this disclosure, all or some of the operations executed on the electronic device 101 can be executed on another or multiple other electronic devices (such as the electronic devices 102 and 104 or server 106). Further, according to certain embodiments of this disclosure, when the electronic device 101 should perform some function or service automatically or at a request, the electronic device 101, instead of executing the function or service on its own or additionally, can request another device (such as electronic devices 102 and 104 or server 106) to perform at least some functions associated therewith. The other electronic device (such as electronic devices 102 and 104 or server 106) is able to execute the requested functions or additional functions and transfer a result of the execution to the electronic device 101. The electronic device 101 can provide a requested function or service by processing the received result as it is or additionally. To that end, a cloud computing, distributed computing, or client-server computing technique may be used, for example. While FIG. 1 shows that the electronic device 101 includes the communication interface 170 to communicate with the external electronic device 104 or server 106 via the network 162, the electronic device 101 may be independently operated without a separate communication function according to some embodiments of this disclosure.

The server 106 can include the same or similar components as the electronic device 101 (or a suitable subset thereof). The server 106 can support to drive the electronic device 101 by performing at least one of operations (or functions) implemented on the electronic device 101. For example, the server 106 can include a processing module or processor that may support the processor 120 implemented in the electronic device 101. As described below, the server 106 may be used to detect and characterize stress using physiological sensors.

Although FIG. 1 illustrates one example of a network configuration 100 including an electronic device 101, various changes may be made to FIG. 1. For example, the network configuration 100 could include any number of each component in any suitable arrangement. In general, computing and communication systems come in a wide variety of configurations, and FIG. 1 does not limit the scope of this disclosure to any particular configuration. Also, while FIG. 1 illustrates one operational environment in which various features disclosed in this patent document can be used, these features could be used in any other suitable system.

Figure 2:
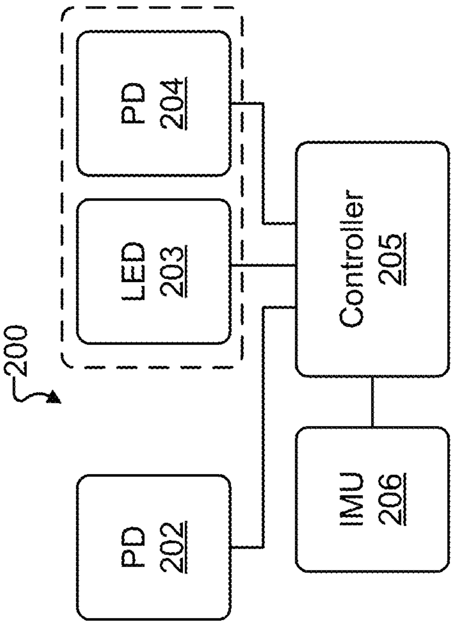
FIG. 2 illustrates exemplary sensing portions of a user device in accordance with this disclosure.

FIG. 2 illustrates exemplary sensing portions 200 of a user device in accordance with this disclosure. The embodiment of the sensing portions 200 shown in FIG. 2 is for illustration only. Other embodiments of the sensing portions 200 could be used without departing from the scope of this disclosure. For simplicity and clarity, only so much of the user device as is necessary to understand the present disclosure is depicted and described. For example, the user device including sensing portions 200 may be an earbud. Although not shown, those skilled in the art will understand that such an earbud will typically include a housing, a speaker, and optionally a microphone. However, the present disclosure encompasses earbuds including those features, as well as features explicitly depicted and described.

FIG. 2 illustrates sensing portions 200 of an earbud, which may constitute one of first and second external electronic devices 102 and 104. Sensing portions 200 include a first photodetector (PD) 202, a light emitting diode (LED) 203, and a second photodetector (PD) 204. LED 203 and PDs 202, 204 are coupled to and controlled by a controller 205 (for example, a microcontroller). The LED 203 emits light onto the adjacent skin of the subject, and the first and second PDs 202, 204 detect the emitted light after reflection off the subject's skin and/or tissue located a shallow distance below that skin. By pulsing the light emitted from LED 203 and measuring reflections of such pulsed light using PDs 202, 204, the optical components of sensing portions 200 may function as a photo plethysmograph. Emitting infrared (IR) light from LED 203 will allow the optical components of sensing portions 200 to measure body temperature. Sensing portions 200 may also include an inertial measurement unit (IMU) 206 (for example, a multi-axis accelerometer) coupled to and providing measurements to controller 205 from which head movement can be determined.

Figure 3:
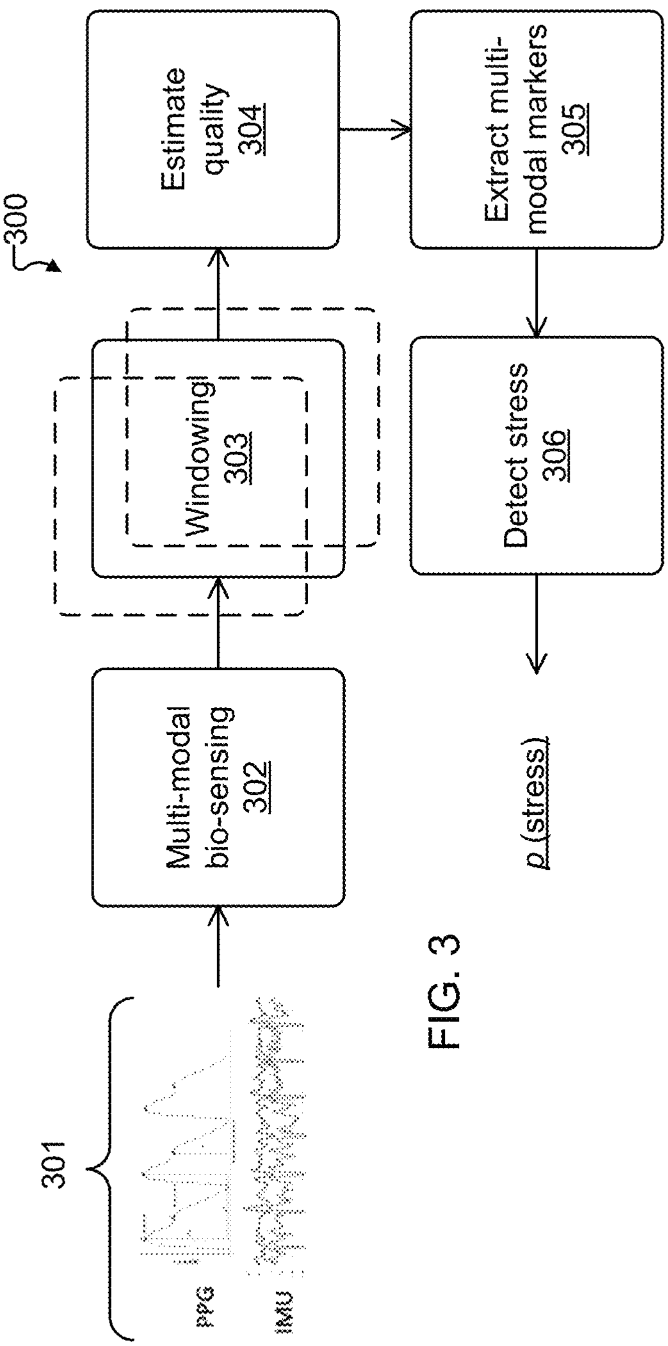
FIG. 3 illustrates an example process flow for continuous stress detection using multi-modal biosensing in accordance with this disclosure.

FIG. 3 illustrates an example process flow 300 for continuous stress detection using multi-modal biosensing in accordance with this disclosure. For ease of explanation, the process flow 300 shown in FIG. 3 is described as being implemented on or supported by one or more components in the network configuration 100 of FIG. 1, such as the electronic device 101, the server 106, or both, and one or more of first and second external electronic devices 102 and 104. However, the process flow 300 shown in FIG. 3 could be used with any other suitable device(s) and in any other suitable system(s).

FIG. 3 depicts a high-level pipeline and core aspects of the embodiment for the process flow 300, including steps of stress detection performed and characterization models utilized. In this embodiment, the system is assumed to utilize a single wearable device for purposes of stress detection. Process flow 300 includes the functional components depicted in FIG. 3, which includes multi-modal physiological bio-sensing 302. This disclosure utilizes a wearable device that is placed on and/or in the body to capture multi-modal physiological biomarkers. In one embodiment described herein, the algorithms are based on earbud sensing as an example use case. The earbud is positioned to capture photoplethysmography (PPG) due to the thinner skin of the human ear. The earbud can also capture head motion due to breathing. Moreover, the earbud can also be used to capture core body temperature. Stressors are known to generally affect heart rate, blood flow, breathing, and body temperature. Accordingly, multi-modal physiological bio-sensing 302 captures photoplethysmography (PPG) and IMU signals 301.

The continuous sensor data captured by multi-modal physiological bio-sensing 302 is segmented into windows, by windowing 303. One embodiment segments the data into 1-minute windows to continuously assess stress minute by minute. However, as illustrated, and depending on the nature of the application, windowing 303 can alternatively or concurrently apply different window sizes to assess the stress, including a smaller window such as 30 seconds (s), or a larger, 5-minute or longer window. In another embodiment, smaller windows may be considered in the first layer, and then majority voting taken over longer windows.

Signal quality has a significant impact on stress detection accuracy. Signal quality can be affected by poor attachment, motion artifact(s), and/or missing samples. Quality estimation 304 in the exemplary embodiment of FIG. 3 detects whether the earbud is worn or not, whether the PPG signal quality is above the acceptable threshold, and whether the signal includes possible motion artifacts based on motion sensor (IMU) data. Motion artifacts can be filtered out using signal-to-noise ratio (SNR) estimation and/or energy estimation derived from accelerometer data. Since breathing motion is more subtle, compared to the noise, quality estimation 304 detects not only the noise in the signal but also motion artifacts when the SNR or energy estimated by the accelerometer is beyond the threshold. Quality estimation 304 can further detect the outliers in peak-to-peak distance (inter-beat interval or "IBI") based on physiological response to activity and stress. Based on the results of quality estimation 304, the process flow 300 proceeds with extraction of multi-modal biomarkers 305.

Figure 4:
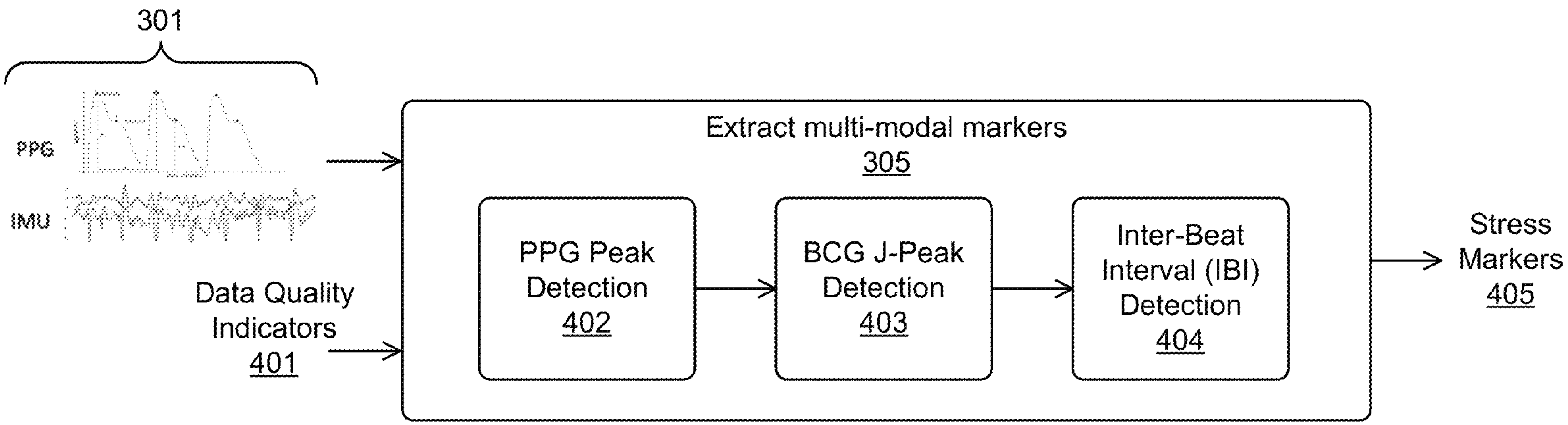
FIG. 4 is an expanded view of a multi-modal stress biomarker extraction pipeline within the process flow of FIG. 3 in accordance with this disclosure.

FIG. 4 illustrates an expanded view of a multi-modal stress biomarker extraction pipeline within the process flow 300 of FIG. 3 in accordance with this disclosure. Multi-modal biomarkers extraction 305 may operate on the raw multi-modal physiological bio-sensing signals 301, as well as data quality indicators 401 from quality estimation 304. Multi-modal biomarkers extraction 305 extracts cardio-respiratory biomarkers. In one embodiment, the cardio-respiratory biomarkers may be computed using multi-modal earbud sensors. First, multi-modal biomarkers extraction 305 removes trends in the PPG signal, detects blood volume or PPG peaks 402, detects BCG J peaks 403 (described further below), and computes or detects inter-beat interval (MI) 404, then outputs stress markers 405. Multi-modal biomarkers extraction 305 further detects outlier IBI due to missed peak or spurious peaks. Multi-modal biomarkers extraction 305 then extracts heart rate (HR), time domain heart rate variability including: standard deviation of NN (SDNN, where "NN" intervals means the time between two successive heartbeats); root mean square of the successive differences (RMSSD); the number of pairs of successive NN intervals that differ by more than 50 milliseconds (ms) (NN50) and the proportion of NN50 divided by the total number of NN intervals (PNN50; mean IBI; frequency domain heart rate variability including respiratory sinus arrythmia (RSA); low frequency/high frequency (LF/HF) ratio; and non-linear heart rate variability including standard deviation of Poincare plot perpendicular to the line-of-identity (SD1), standard deviation of the Poincare plot along the line-of-identity (SD2), and the ratio of SD1 and SD2.

The motion sensor (IMU) data can be used for the following purposes:

- Capturing lung motion to estimate breathing biomarkers (breathing rate and inhale-exhale ratio). Breathing expands and contracts the lung, and lung expansion and contraction moves the shoulder and the head. Motion sensors in head- or neck-worn wearables captures such motion, and multi-modal biomarkers extraction 305 can extract the breathing motion (which happens in a different frequency from the heart motion) and non-breathing head motion, and then estimate breathing rate and inhale-exhale ratio—which are correlated with stress.
- Capturing subtle ballistic motion due to heart pumping the blood, to estimate (when combined with PPG data) heart rate, heart rate variability, and hemodynamic biomarkers such as cardiac output (CO), stroke volume (SV), pulse transit time (PTT). Similar to lung motion, heartbeat motion while pumping the blood shakes the head and body, although this motion happens in much higher frequency compared to lung motion. Moreover, this motion leaves a unique signature in motion sensor data which is called ballistocardiograph (BCG), a measure of the ballistic forces generated by the heart which has a particular structure called I-J-K complex (similar to Q-R-S complex in the ECG signal). Multi-modal biomarkers extraction 305 identifies the I-J-K template, and detects the BCG J peak 403. The amplitude of the J peak correlates with the volume of the blood pumped by the heart. Multi-modal biomarkers extraction 305 estimates cardiac output (CO)=SV×HR 1/min. Pulse Transit Time (PTT) is computed as the time difference between the J peak and the PPG peak.
- Helping detect motion artifacts due to head or body motion that interferes with the biomarker estimation and determine the quality of the data. Motion due to moving the head due to daily activities including physical activity or work related activities can be detected using the IMU sensor. Multi-modal biomarkers extraction 305 considers head or body motion signal effects as motion artifacts and adjust the estimation according to the SNR or intensity of the motion estimated from the signal energy and entropy.

Figure 5A:
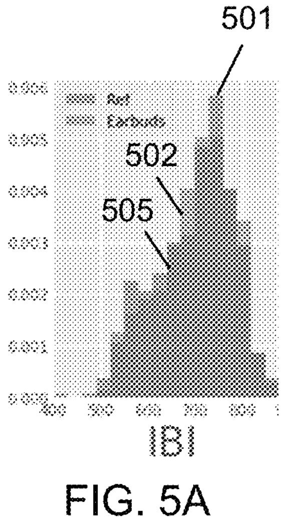
FIGS. 5A and 5B illustrate plots corresponding to IBI quality in accordance with this disclosure.
Figure 5B:
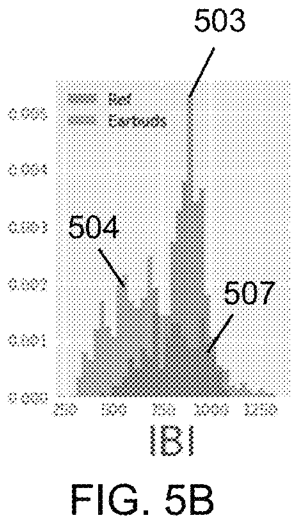
Figure 6:
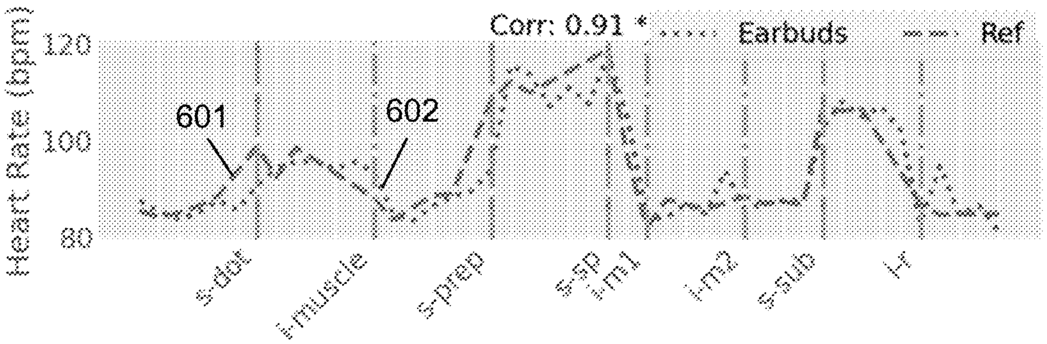
FIG. 6 illustrates overlapping plots corresponding to heart rate comparison with a reference heartrate in accordance with this disclosure.

FIGS. 5A and 5B illustrate plots corresponding to inter-beat-interval (MI) quality in accordance with this disclosure, and FIG. 6 illustrates overlapping plots corresponding to heart rate measurements 602 compared with a reference heartrate 601, in beats per minute (bpm), in accordance with this disclosure. Multi-modal biomarkers extraction 305 calculates probabilistic quality index for the estimated IBI by comparing the IBI distribution 502, 504 estimated from the earbud measurements with a corresponding reference IBI distribution 501, 503 (where the darkest-shading represents overlap 505, 507 between estimated IBI distribution 502, 504 and the corresponding reference IBI distribution 501, 503). From the training dataset, there is an expected distribution of the IBI for the baseline (non-stress) and the stress arousal, which are reference IBI distributions 501, 503. Multi-modal biomarkers extraction 305 calculates the deviation of the estimated IBI distributions 502, 504 from the expected distributions 501, 503 as the quality index. FIGS. 5A and 5B show the IBI quality comparison and FIG. 6 shows the heart rate comparison between the estimated and the reference data.

Figure 7B:
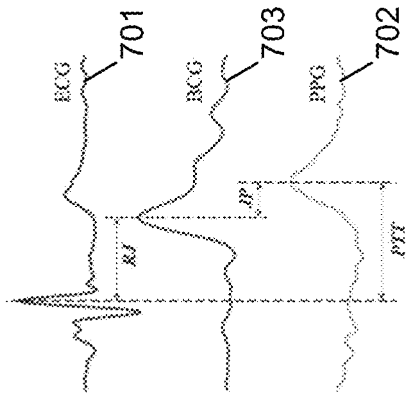
FIGS. 7A and 7B illustrate plots corresponding PPG, BCG, and ECG biomarkers, used to estimate PTT within multi-modal biomarkers extraction in accordance with this disclosure.
Figure 7A:
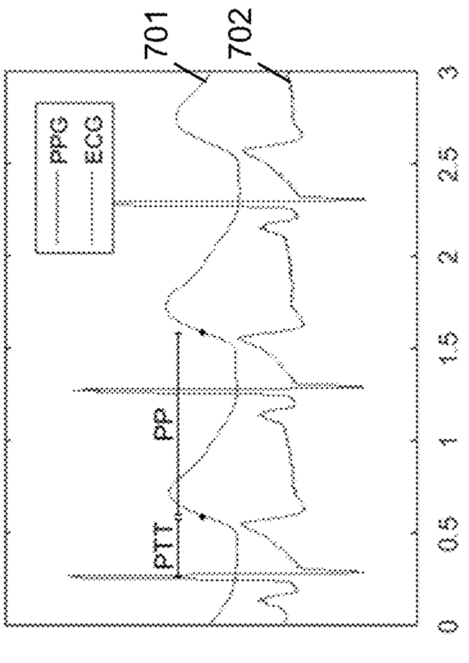

FIGS. 7A and 7B illustrate plots corresponding to PPG, BCG, and ECG biomarkers, used to estimate PTT within multi-modal biomarkers extraction 305 by combining the ECG data 701 in addition to PPG data 702 and IMU (BCG) data 703, and estimating blood pressure. Blood pressure is correlated with stress and can vary between the good and bad stress. An exponential model for systolic blood pressure (SBP) is:

$$SBP = A - B \cdot \ln PTT^2,$$

where A and B are constants and can be estimated using linear regression.

In the present disclosure, end-to-end data processing for minute-by-minute stress detection may employ an earbud's physiological signals to derive psycho-physiological signal(s), which are compared against standard psycho-physiological signals for use in autonomic nervous system (ANS) stress response modeling and feature extraction. By way of example, a sympathetic nervous system (SNS) index of −1.44 may indicate stress, while a parasympathetic nervous system (PNS) index of 1.94 may indicate recovery.

Figure 8:
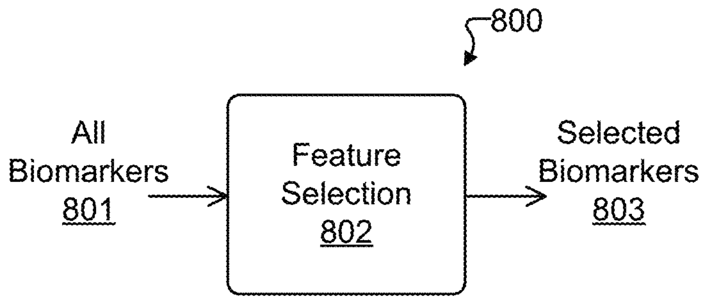
FIG. 8 illustrates an expanded view of biomarker selection for stress detection and characterization within the process flow of FIG. 3 in accordance with this disclosure.
Figure 9:
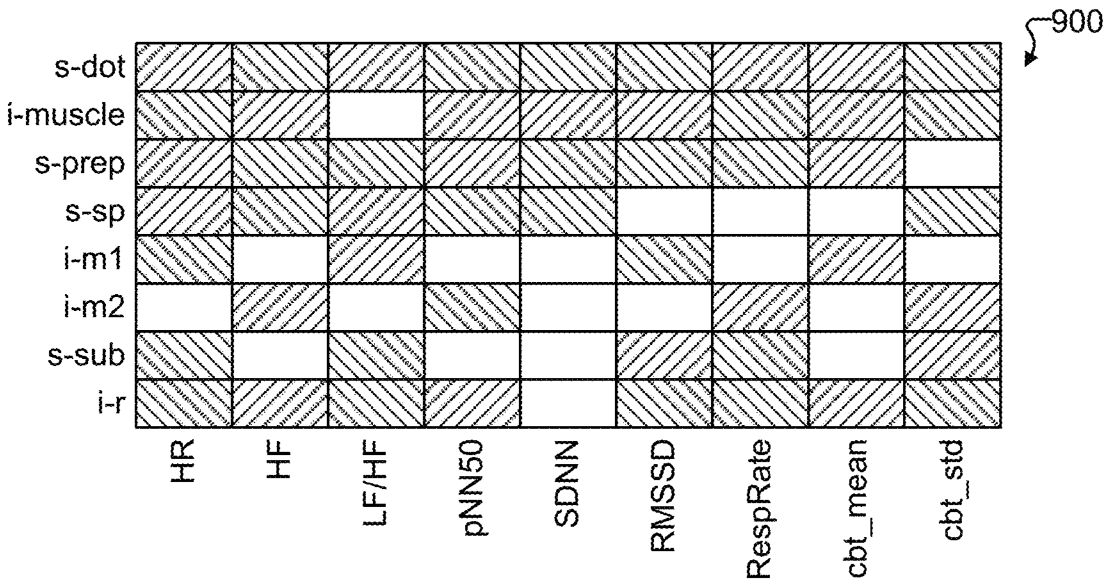
FIG. 9 graphically illustrates biomarker responses to stress and relaxation in accordance with this disclosure.

FIG. 8 illustrates an expanded view 800 of biomarker selection for stress detection and characterization within the process flow of FIG. 3 in accordance with this disclosure. After the cleaning and screening of the physiological features, multi-modal biomarkers extraction 305 further analyzes the trends (increase or decrease) of each feature during stress and relaxation activities. FIG. 9 graphically illustrates biomarker responses 900 to stress and relaxation in accordance with this disclosure, where diagonal fill in one direction represents increase while diagonal fill in the other direction represents decrease, and darkness of the fill correlates to the amount of increase/decrease. From all biomarkers 801, the physiological features that show stronger response and in the expected direction are selected by feature selection 802 to determine selected biomarkers 803. In FIG. 9, the x-axis indicates biomarker types, and the y-axis indicates activity types. The stress activities are denoted by the letter "s" and the relaxation activities are denoted by the letter "i." For example, the biomarker RMSSD between successive inter-beat-intervals describes short-term heart rate variability (HRV). Decreased RMSSD value indicates increased stress, which means that the stress activities are expected to have decreased RMSSD values while relaxation activities are expected to have increased RMSSD values. Since the RMSSD response is consistent with the expected changes across various stress activities and relaxation activities, HRV features may be selected for training a model used to detect stress 306.

Figure 10:
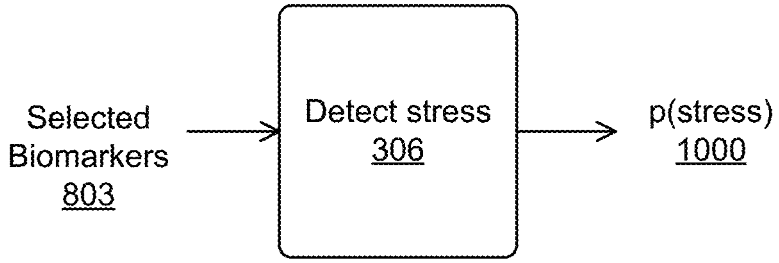
FIG. 10 illustrates an expanded view of biomarker selection for stress probability detection within the process flow of FIG. 3 in accordance with this disclosure.

FIG. 10 is an expanded view of biomarker selection for stress probability detection within the process flow of FIG. 3. To detect physiological stress arousal, stress detector 306 utilizes a model to compute the probability of stress p(stress) through stress and non-stress classification on the extracted biomarkers 803. Positive (stress) class is assigned to the biomarker features extracted from the known stressors including dot-tracking, speech, and mental arithmetic tasks. Negative (non-stress) class is assigned to features from the baseline and relaxation tasks including calm music and resting baseline. In one instance, this approach results in 473 data rows, where each data row represents features extracted from one minute of continuous physiological data. Among the data rows, 186 data rows were in the positive category and 287 were in the negative category. To develop a generic stress detector, the present disclosure uses a leave-one-subject-out (LOSO) cross-validation experiment, where both the stress and non-stress data from one subject are left out for testing. This embodiment trains a machine learning model called Random Forest classifier with remaining subjects' data, and then applies the model on the left-out subject's data, which is unseen to the model. This approach allows estimation of the model accuracy in being more generalizable to future unknown subjects. To avoid overfitting of the model, tree depth is kept low (maximum depth as 4) and the Random Forest model uses only 100 estimators, using the same parameters for training the model on the reference data and the earbud data for performance comparison. Another embodiment can train other machine learning models such as a support vector machine, a gradient boosted tree, adaptive boosting, logistic regression or deep neural learning models such as convolutional neural network (CNN), recurrent neural network (RNN), or the like.

Figure 11:
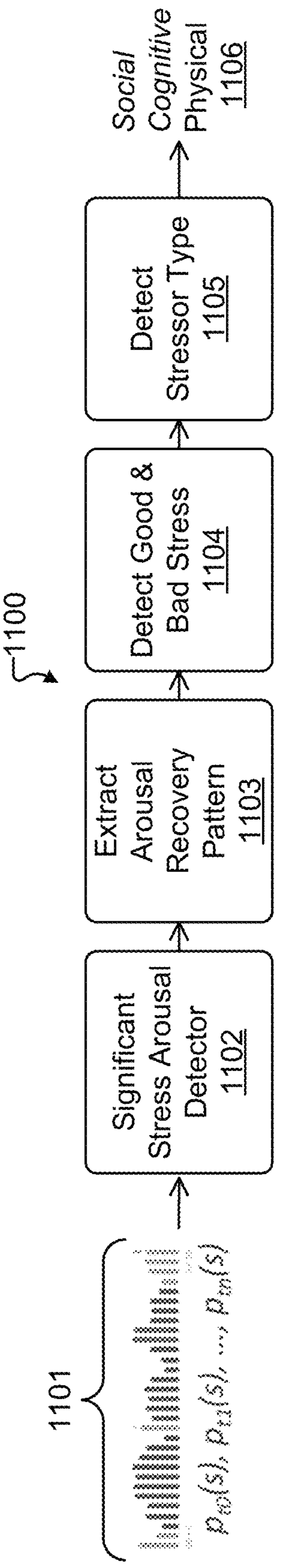
FIG. 11 illustrates an example process flow for detecting stress valence and type of the stressor in accordance with this disclosure, as part of detecting stress within the process flows of FIGS. 3 and 10 in accordance with this disclosure.

FIG. 11 illustrates an example process flow 1100 for detecting stress valence and type of the stressor in accordance with this disclosure, as part of detecting stress within the process flows of FIGS. 3 and 10. For ease of explanation, the process flow 1100 shown in FIG. 11 is described as being implemented on or supported by one or more components in the network configuration 100 of FIG. 1, such as the electronic device 101, the server 106, or both, and one or more of first and second external electronic devices 102 and 104. However, the process flow 1100 shown in FIG. 11 could be used with any other suitable device(s) and in any other suitable system(s).

For stress arousal categorization, good or bad stress and other type(s) of stress arousal are identified from the stress response time series data such as $p_{t0}(s)$, $p^{t1}(s)$, . . . $p_{tn}(s)$ 1101. Stress arousal characterization can involve detecting significant stress arousal segments 1102 in continuous time-series data. Significant arousal can be defined as the level, duration, and number of modalities of arousal. One embodiment can consider the sympathetic system response such as heart rate arousal, while another embodiment can consider heart rate, heart rate variability, and breathing rate responses. Another embodiment can fuse the biomarkers into an SNS index and a PNS index to detect the significant arousal segments.

Arousal recovery pattern extraction 1103 determines arousal and recovery patterns. Four important points in the physiological response cycle are identified and utilized detect the elevation pattern and recovery patterns, arousal duration, and total response cycle duration. These markers can be determined for each of the physiological responses.

Good and bad stress detection 1104 determines unhealthy (bad) stress response from healthy (good) response. The physiological responses can distinguish unhealthy (bad stress) from healthy responses (good stress) by comparing the current arousal patterns with the expected pattern. The patterns can further be characterized into social, cognitive, and physical stressor.

Stressor type detection 1105 determines the type of stressor 1106 for the bad stress responses. This embodiment further analyzes the physiological responses for the bad stress segments to determine whether the arousal is from a social stressor, cognitive stressor, the physical stressor or the like. The stress mitigating intervention can then be tailored based on the detected stressor type.

Figure 12:
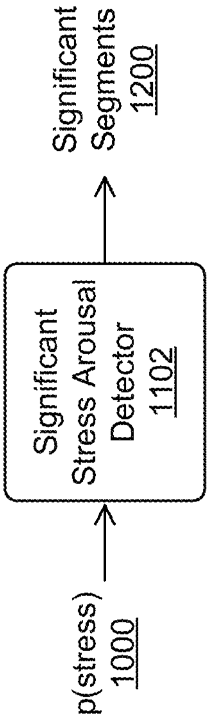
FIGS. 12 and 13 illustrate further details of significant arousal segmentation within the process flow of FIG. 11 in accordance with this disclosure.
Figure 13:
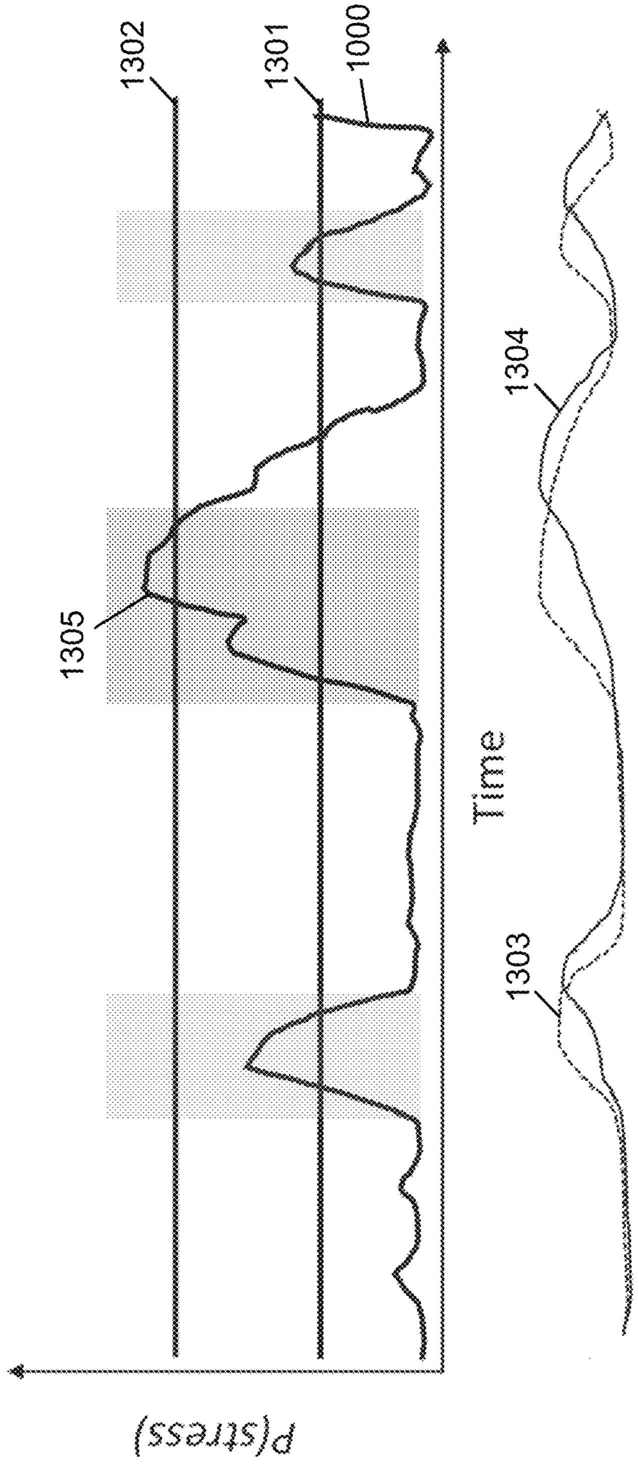

FIGS. 12 and 13 illustrate further details of significant arousal segmentation within the process flow of FIG. 11. FIG. 13 illustrates significant arousal detection in a stress timeseries data 1000. As illustrated in FIG. 12, significant stress arousal detector 1102 receives stress timeseries data 1000 and determines significant segments 1200. Significant arousal segments 1200 in a stress timeseries data 1000 are detected by defining significant stress arousal as arousal above the baseline 1301 or the pre-defined arousal threshold 1302 over a certain duration (e.g., >5 minutes). The candidate arousal segments are first detected using the following formula for recursively calculating the ecological momentary assessment (EMA) of a series Y:

$$S_t = \begin{cases} Y_1, & t = 1 \\ \alpha \cdot Y_t + (1-\alpha) \cdot S_{t-1} & t > 1 \end{cases}$$

where $Y_t$ is the value at a time period t and $S_t$ is the value of the EMA at any time period t. The coefficient α represents the degree of weighting decrease, a constant smoothing factor between 0 and 1. A higher a discounts older observations faster. A moving average convergence divergence (MACD) line 1303 is determined as:

$$MACD\ \text{Line} = EMA_{slow} - EMA_{fast},$$

and a signal line 1304 is determined as:

$$\text{Signal Line} = EMA\ \text{of}\ MACD\ \text{Line}.$$

In the example implementation is shown in FIGS. 12 and 13 where several candidate arousals are identified from based on the continuous stress timeseries data. However, one of the candidate arousals 1305 is identified as a significant arousal since the intensity and the duration of this segment is above the thresholds 1301, 1302. One embodiment can further analyze and extract higher level features to identify the pattern of the segment. Another embodiment can combine more than one segments in the vicinity before further analysis.

Figure 14:
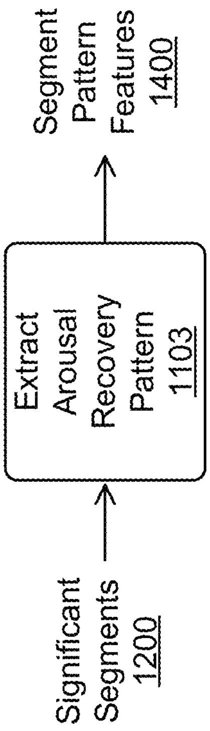
FIGS. 14, 15, and 16 illustrate further details of feature extraction from an arousal segment within the process flow of FIG. 11 in accordance with this disclosure.
Figure 15:
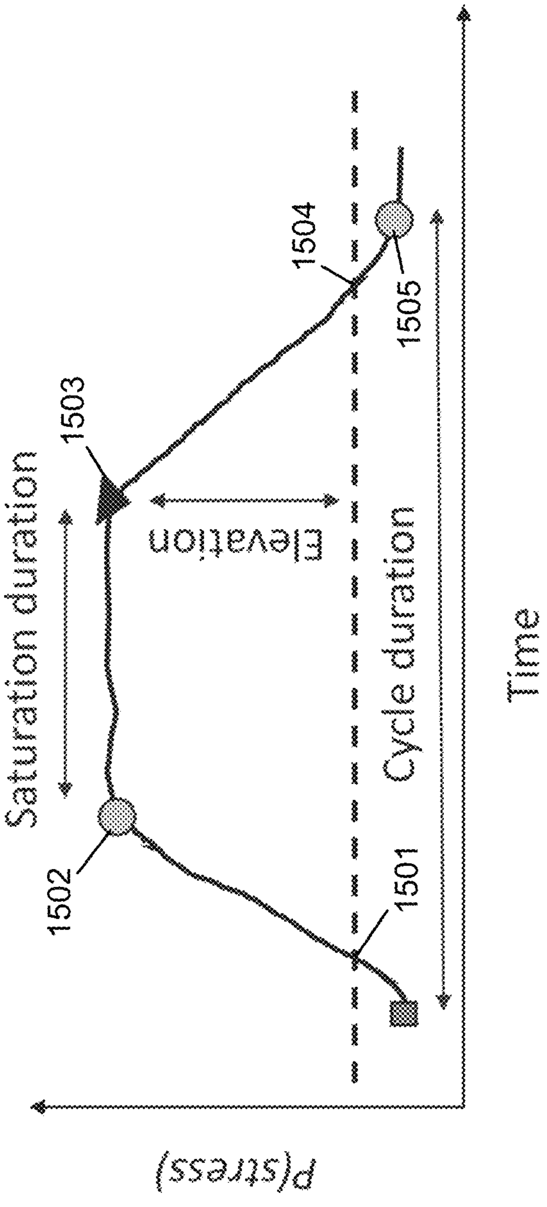
Figure 16:
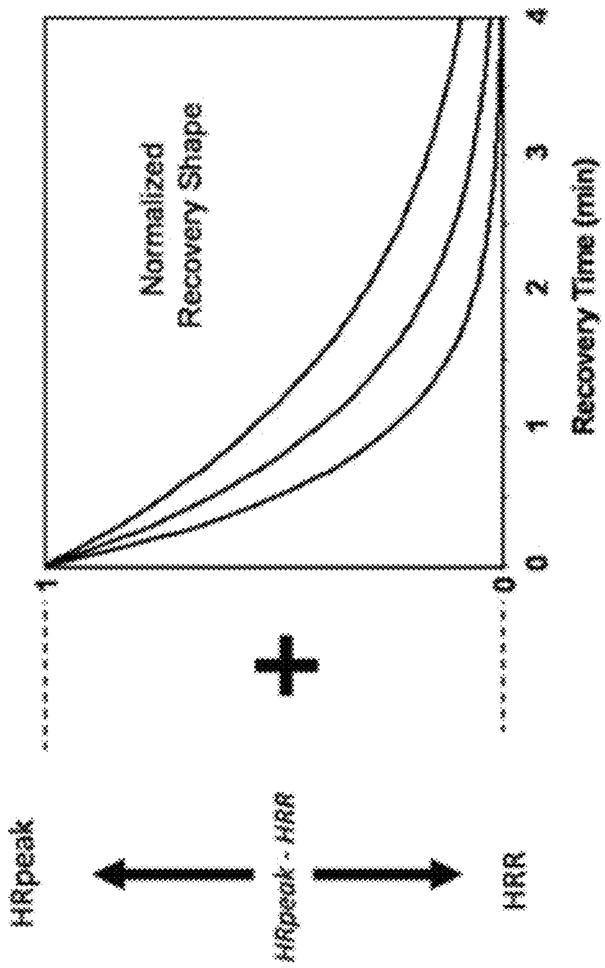

FIGS. 14, 15, and 16 illustrate further details of feature extraction from an arousal segment within the process flow of FIG. 11. FIG. 15 illustrates heartrate as a function of time, while FIG. 16 is an example of recovery rate feature estimation for heart rate biomarker. Extraction of arousal recovery pattern features is based on first identifying four important fiducial points in a significant stress arousal segment: (1) arousal initiation point 1501, (2) peak arousal 1502 and saturation point 1503, (3) recovery initiation point 1504, and (4) end of recovery 1505. Those points may be detected by computing the slope of the stress likelihood timeseries data within the segment and the temporal location. Then segment pattern features 1400 may be extracted, including rate of arousal, rate of recovery, arousal segment duration, stress saturation duration, intensity of arousal as the elevation from the baseline, similarity between the expected and the current pattern, and the like. These features should be different in healthy and unhealthy stress responses, and can be also useful for detecting the stressor type. As illustrated by FIG. 16, heartrate recovery (HRR) may be determined by:

$$HRR = HR_{Rest} + (HR_{Peak} - HR_{Rest})e^{-\frac{t-t_0}{\tau}},$$

$$t - t_0 = \tau\ \ln\frac{HR_{Peak} - HR_{Rest}}{HRR - HR_{Rest}},$$

where $t_0$ corresponds to the recovery initiation point 1403, t corresponds to the end of recovery 1404, τ is a decay constant, $HR_{Peak}$ is the peak heartrate (e.g., at the recovery initiation point 1403), and $HR_{Rest}$ is resting heartrate (e.g., the end of recovery 1404).

Figure 17A:
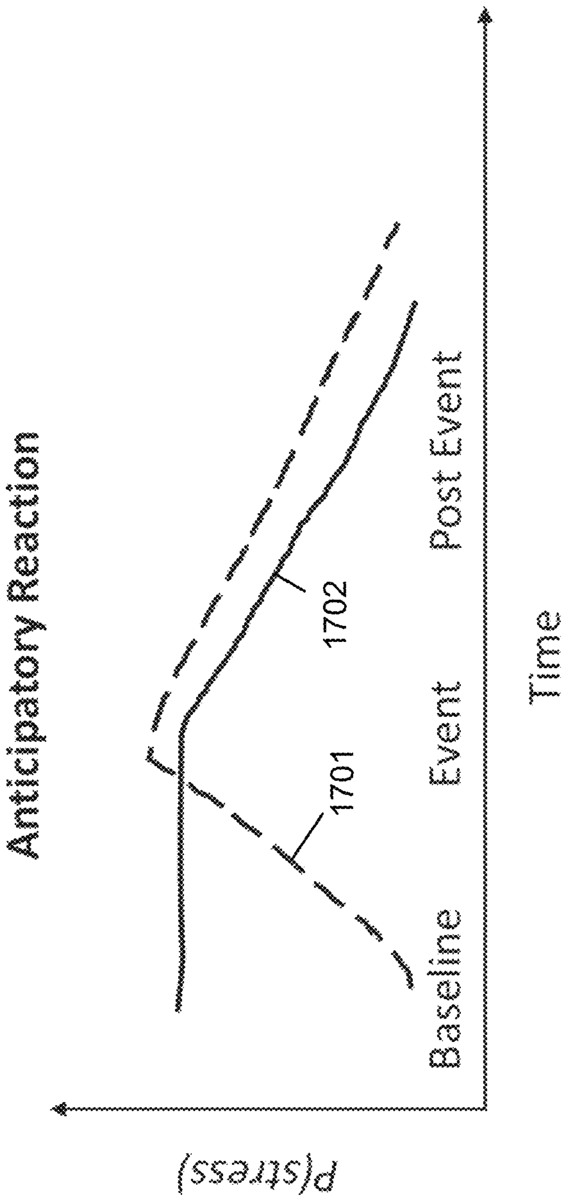
FIGS. 17A through 17D illustrate arousal and recovery patterns for healthy and unhealthy responses, for feature extraction from an arousal segment within the process flow of FIG. 11 in accordance with this disclosure.
Figure 17B:
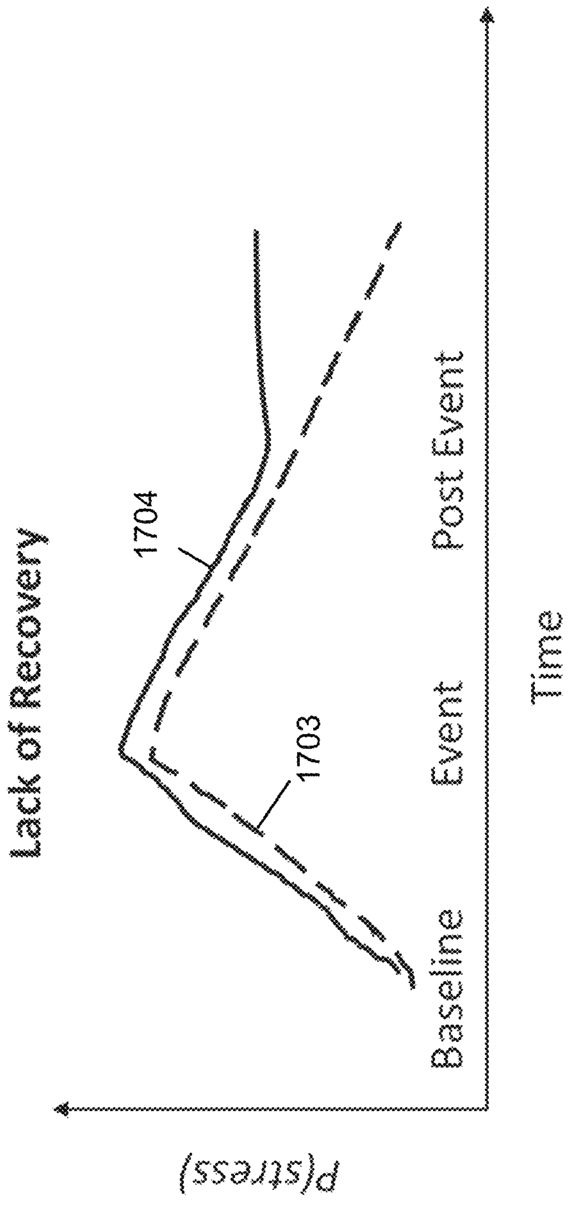
Figure 17C:
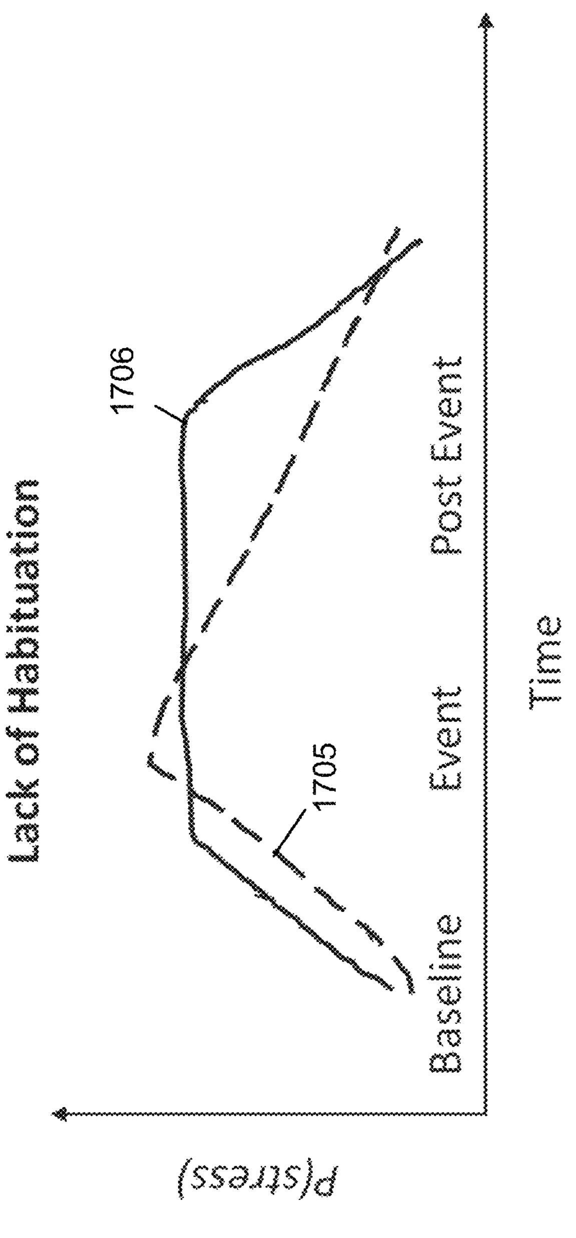
Figure 17D:
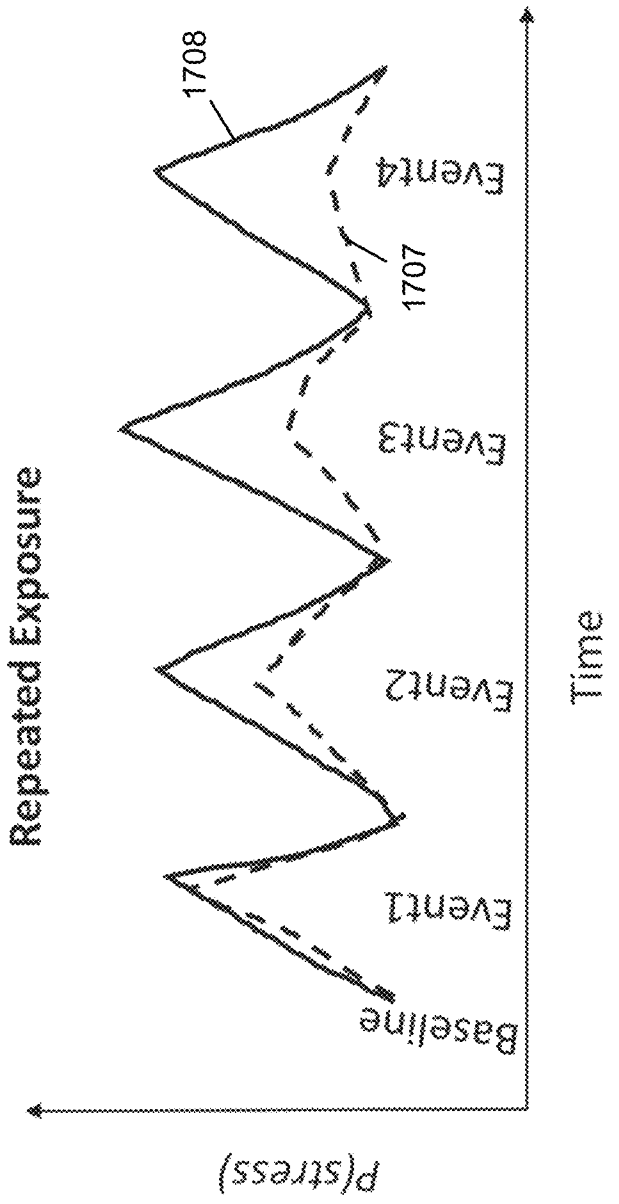

FIGS. 17A through 17D illustrate arousal and recovery pattern for healthy and unhealthy responses, for feature extraction from an arousal segment within the process flow of FIG. 11 in accordance with this disclosure. FIG. 17A illustrates healthy anticipatory reaction 1701 and unhealthy anticipatory reaction 1702; FIG. 17B illustrates healthy lack of recovery 1703 and unhealthy lack of recovery 1704; FIG. 17D illustrates healthy lack of habituation 1705 and unhealthy lack of habituation 1706; and FIG. 17D illustrates healthy repeated exposure 1707 versus repeated exposure 1708. Templates of expected arousal recovery patterns in the arousal segment can be defined from annotated training data using the following equation:

$$T[n] = \frac{1}{K}\sum_{k=1}^{K} Env_k[n],\ \forall\ n \in [1, N],$$

where T[n] is the template (among N templates) derived from K different example segments, and $Env_k$ is the shape of the kth example segment. Similarity between the templates and the current arousal segment may be calculated using the following equation:

$$D = \sum_{i=1}^{M} \|Env_c[i] - T[i]\|,$$

where $Env_c$ is the current arousal segment of interest and M is the number of data points in the current segment. For example, there are eight templates in FIGS. 17A through 17D. Healthy anticipatory reaction 1701, healthy lack of recovery 1703, healthy lack of habituation 1705, and healthy repeated exposure 1707 are templates representing healthy arousal and recovery patterns in response to stress. Unhealthy anticipatory reaction 1702, unhealthy lack of recovery 1704, unhealthy lack of habituation 1706, and unhealthy repeated exposure 1708 are templates representing unhealthy arousal and recovery patterns in response to stress. The distance between each of the templates T [i] to biomarker features pf a user is computed, and the template with the smallest distance is determined to have the closest pattern to the biomarker features. If the template with the closest pattern is a template representing an unhealthy arousal and recovery pattern, the user's response to stress is determined to be an unhealthy response. If the template with the closest pattern is a template representing a healthy arousal and recovery pattern, the user's response to stress is determined to be a healthy response.

Figure 18:
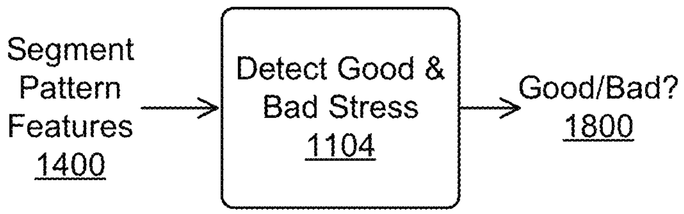
FIGS. 18 and 19A through 19F illustrate further details of good or bad stress determination within the process flow of FIG. 11 in accordance with this disclosure.

FIGS. 18 and 19A-19F collectively illustrate further details of good/bad stress determination within the process flow of FIG. 11. As shown in FIG. 18, segment pattern features 1400 are used to evaluate stress as healthy or unhealthy, to provide an indication 1800 of the type of stress detected. Detection of good and bad stress 1104 takes the pattern features and the similarity features into consideration and to determine whether the current arousal segment will be categorized as the good (healthy) or bad (unhealthy)

stress arousal. One embodiment can compare only the arousal pattern or recovery pattern to determine the good and bad stress. Another embodiment can take all pattern features into consideration. Another embodiment can also consider the physiological biomarkers such as heart rate variability, cardiac output, stroke volume, pulse transit time, and estimated blood pressure into consideration to determine the good and bad stress responses.

Figure 19A:
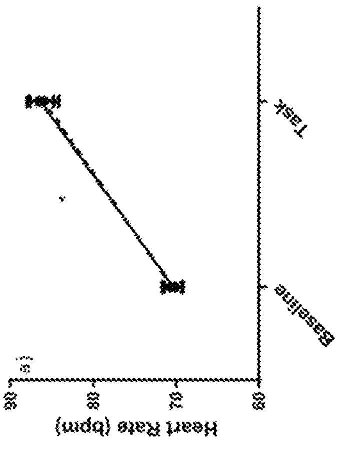
Figure 19B:
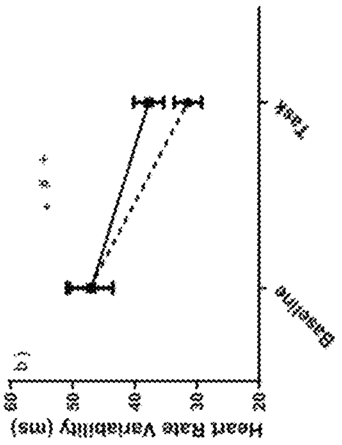
Figure 19C:
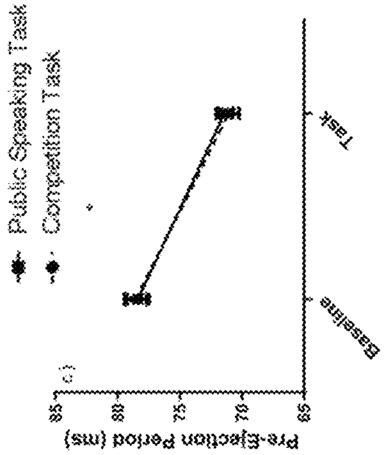
Figure 19D:
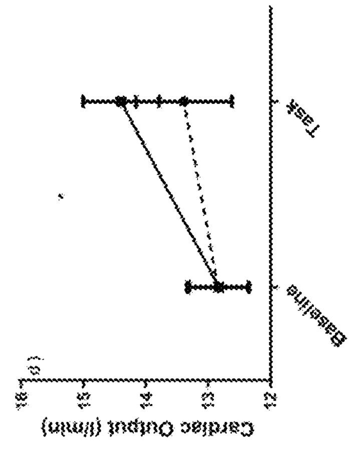
Figure 19E:
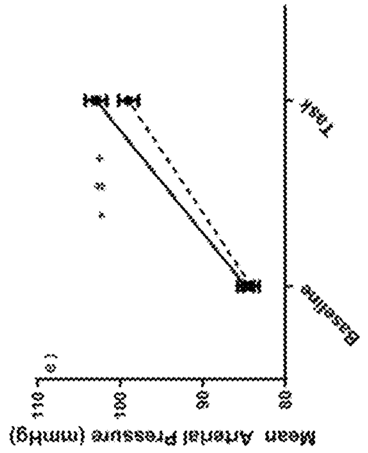
Figure 19F:
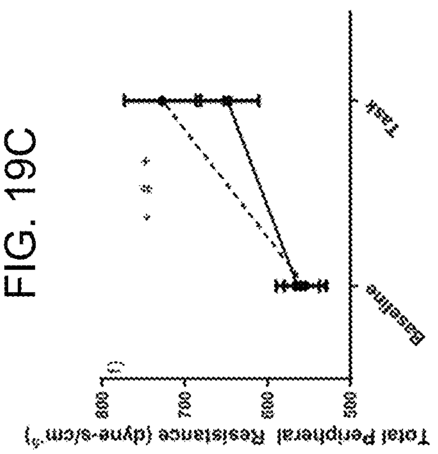

FIGS. 19A through 19F illustrate comparative plots of selected multi-modal biomarker responses in two different types of stress: public speaking (solid lines) and a competitive task (dashed lines). Each plot illustrates the change from baseline resulting from performing the respective task. FIG. 19A illustrates the change in heartrate. FIG. 19B illustrates the change in heartrate variability. FIG. 19C illustrates the change in pre-ejection period (PEP, the time elapsed between electrical depolarization of the left ventricle—QRS on the ECG—and the beginning of ventricular ejection, representing the period of left ventricular contraction with the cardiac valves closed, which is influenced by sympathetic activity and shortens under stress). FIG. 19D illustrates the change in cardiac output. FIG. 19E illustrates the change in mean arterial blood pressure. FIG. 19F illustrates the change in total peripheral resistance.

FIGS. 20 and 21A-21C collectively illustrate further details of stressor type determination within the process flow of FIG. 11. In response to a bad/unhealthy stress judgment 2000 by good/bad stress detection 1104, stressor type detection 1105 analyzes the timeseries stress data and the multi-modal physiological biomarkers in the bad stress segment to determine the type of stressor. Physiological responses during social stress are different from those during cognitive and physical stress. One embodiment can compare the distribution of each individual biomarkers in a stress segment with the pre-trained distribution of the same biomarker from different types of the stressor. Stressor type detection 1105 then takes the majority voting or other ensemble approach to calculate the probability for being social, cognitive, or physical stressor. One embodiment can determine the type of stressor based on the highest probability. Another embodiment can utilize the machine learning or deep learning approach to classify the stressor type.

Figure 21A:
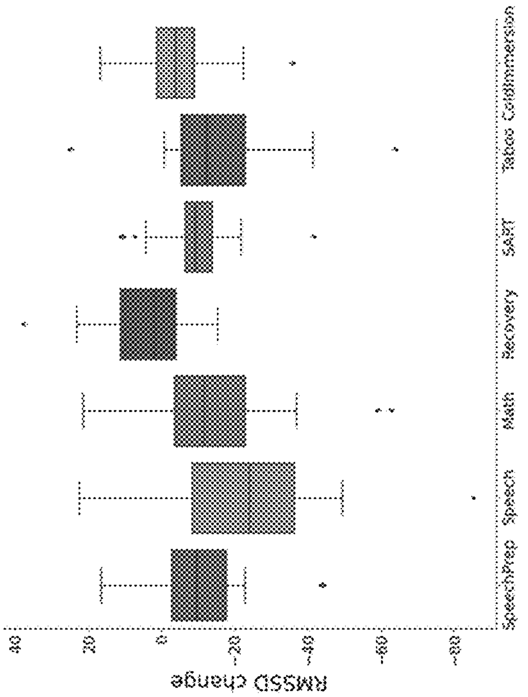
FIGS. 20 and 21A through 21C illustrate further details of stressor type determination within the process flow of FIG. 11 in accordance with this disclosure.
Figure 20:
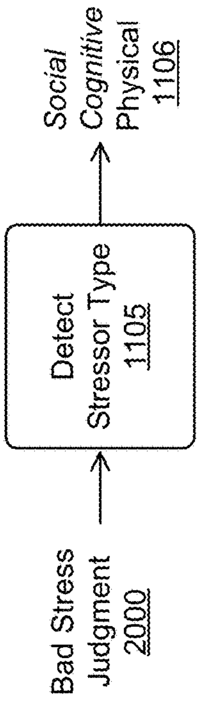
Figure 21C:
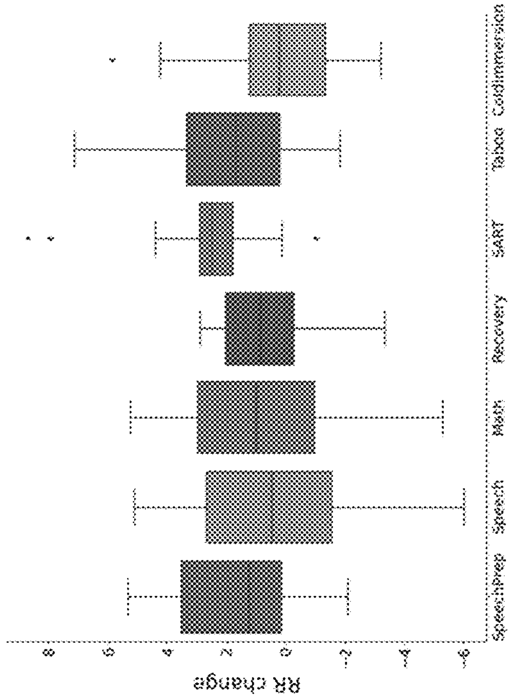
Figure 21B:
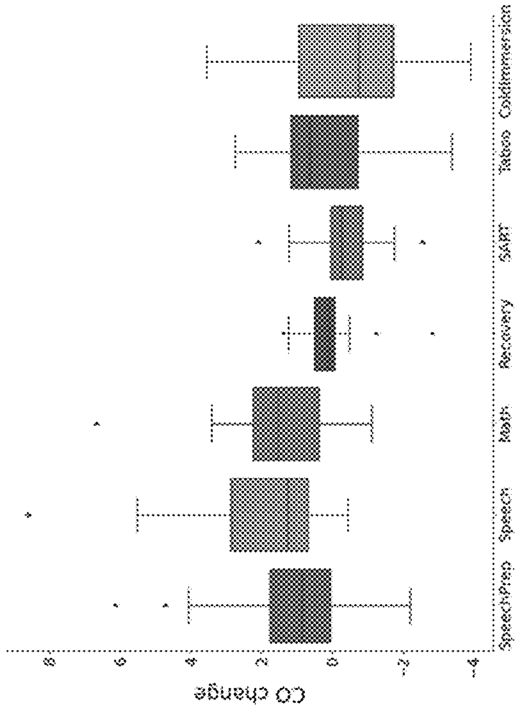

FIGS. 21A through 21C illustrate physiological responses distributions for three different biomarkers: RMSSD change in FIG. 21A; CO change in FIG. 21B; and RR (or NN) interval change in FIG. 21C. In each figure, the distributions are plotted for the same set of social, cognitive, or physical stressors: speech preparation; engaging in speech (e.g., public speaking); performing math calculations; recovery (relaxation); exposure to specific alternation of rhythm in temperature (SART); engaging in a "taboo" activity; and continuous immersion in a cold environment.

Figure 22:
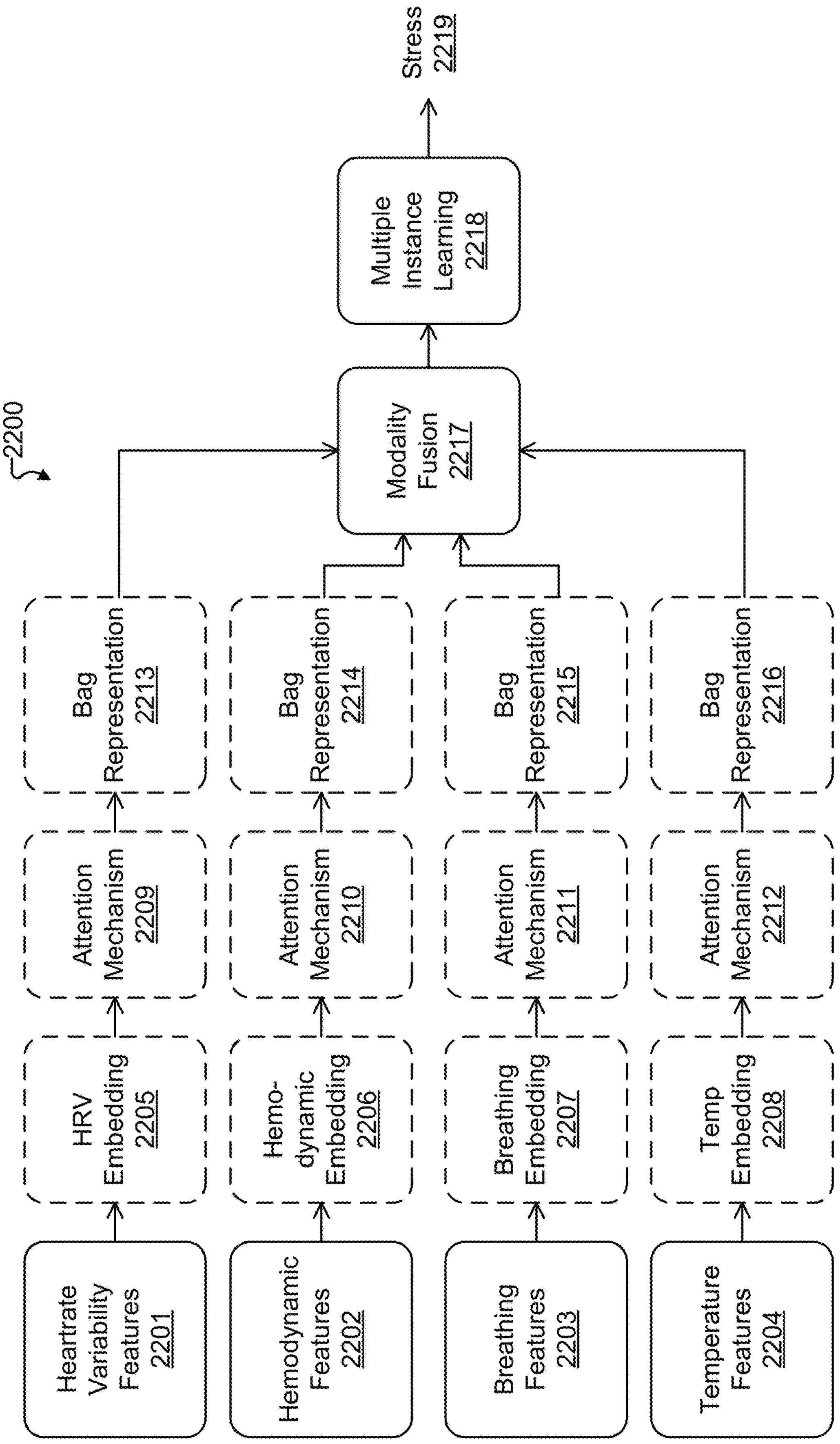
FIG. 22 illustrates an example process flow for stress response categorization using machine learning models in accordance with this disclosure, as an alternative for good and bad stress detection in FIG. 11 in accordance with this disclosure.
Figure 23:
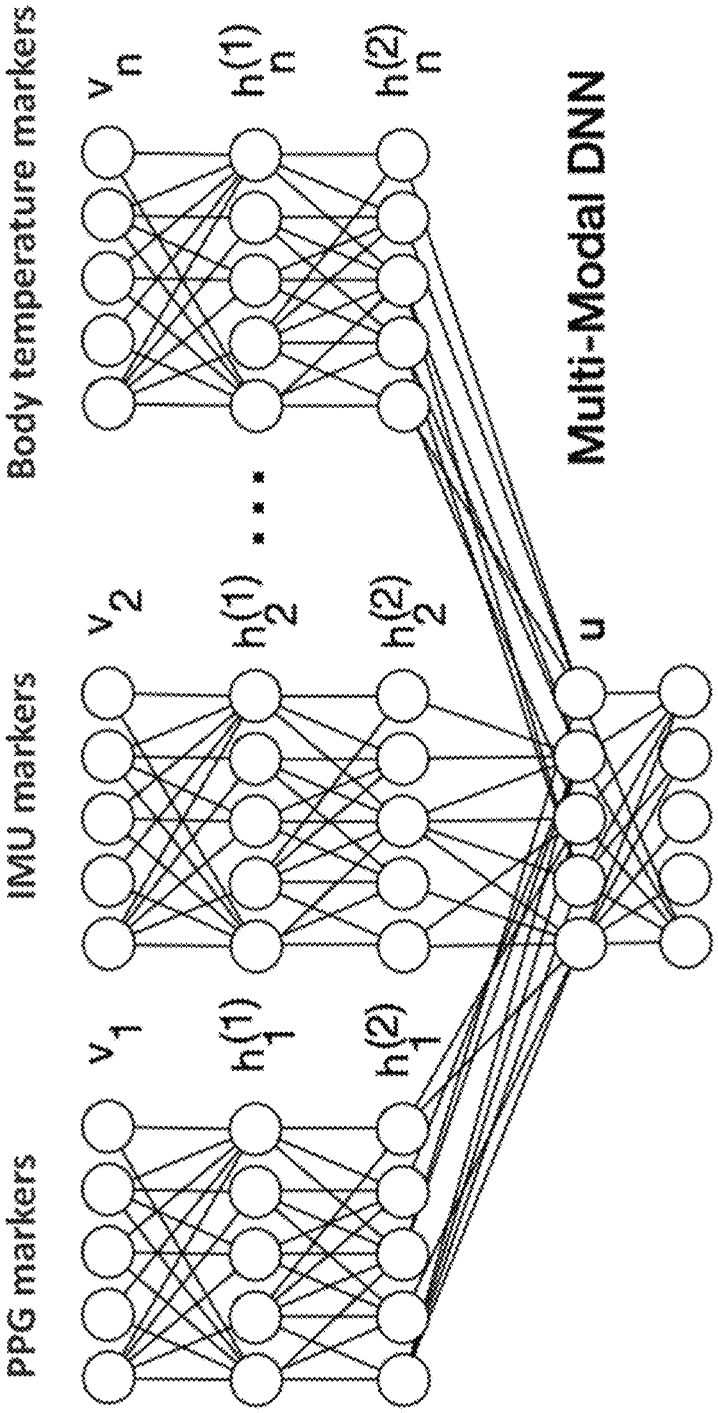
FIG. 23 illustrates an alternative machine learning model to that employed in connection with FIG. 22 in accordance with this disclosure.

FIG. 22 illustrates an example process flow for stress response categorization using machine learning (ML) models in accordance with this disclosure, as an alternative for good and bad stress detection 1104 in FIG. 11. This embodiment utilizes a machine learning approach to detect and characterize stress. Stress response categorization 2200 utilizes an attention-based multiple instance learning model to detect stress and characterize the stress into good or bad, or tag the stress into physical, social, or cognitive type. Stress response categorization 2200 receives biomarker response data for selected features: heartrate variability features 2201, hemodynamic features 2202, breathing features 2203, and temperature feature 2204 in the example shown. Each selected feature has a corresponding embedding layer 2205, 2206, 2207, and 2208, and a corresponding attention mechanism 2209, 2210, 2211, and 2212.

In stress response categorization 2200, the input of a classifier is considered as a bag B of K instances, $B=\{x_1, x_2, \ldots, x_K\}$. Each bag B 2213, 2214, 2215, and 2216 has an associated single binary label Y={no-stress, stress} during training. In another embodiment, each bag B has an associated single binary label Y={good-stress, bad-stress} during training. A negative bag is the extracted feature set from negative baseline or recovery data and the positive bag is the features from the stressor class in the training data. The features can be extracted from smaller windows (e.g., 30 seconds with 20 seconds sliding) to create one instance in each second. Then a one minute bag will include, at most, 60 instances. This embodiment can perform modality specific embeddings to transform a lower dimensional vector for each modality for modality fusion 2217. Stress response categorization 2200 can further generate attention weights $a_{im}$ for each modality, and generate a modality-specific bag embedding $t_m$:

$$t_m = \sum_{i=1}^{k} a_{im} e_{im}, \text{ where } a_{im} = \frac{\exp\{w_m^T \tanh(V_m e_{im}^T)\}}{\sum_{j=1}^{k} \exp\{w_m^T \tanh(V_m e_{jm}^T)\}},$$

where $e_{im}$ is the modality-specific embeddings for i=1, 2, . . . , k, and $w_m$ and $V_m$ are network parameters of the m modality-specific attention mechanism block 2209, 2210, 2211, or 2212. Different modality specific attention blocks 2209, 2210, 2211, and 2212 may learn different attention weights for each instance, enabling the pattern extraction independently from each other modality. Modality fusion block 2217 can capture the cross-modality relationships. Modality fusion block 2217 concatenates all the modality-specific embeddings and generates a new feature vector that encodes pairwise relations among all possible dimensions $f(x_i, x_j)$ of X and the unary relations $g(x_i)$. One embodiment can use embedded gaussian function for $f(x_i, x_j)$ and linear embedding for $g(x_i)$. Each $z_i$ encoding can be computed using the following formula:

$$z_i = \frac{1}{C(x)} \sum_{\forall j} f(x_i, x_j) g(x_i),$$

where C(x) is the normalization factor and C(x)=sum $(f(x_i, x_j))$ for all j. One embodiment can use two or more fully connected layers followed by a sigmoid activation function for the final classification into stress/non-stress or good-stress/bad-stress. One embodiment can extend this approach for multi-class classification for the stressor type (social/physical/cognitive) detection.

This ML approach works with weakly labelled data, extracting modality-specific distinctive patterns for multiple instance learning model 2218 to determine stress and the type of stress 2219. An alternative ML approach embodiment, illustrated in FIG. 23, can take the features from each modality 1 through n to design a modality-specific deep neural network (DNN) that creates a separate branch for each modality and then joins the outputs of those branches using a unifying cross-layer network for stress type detection.

Another embodiment can utilize the acoustic data captured by the earbud or other mobile device(s) to analyze auditory cues related to stress and affect. Another embodiment can include camera data to capture the facial expression for stressor type classification. For example, a smile may indicate the positive arousal while a sad facial expression may indicate negative stress arousal.

In addition to, or in lieu of, the above-described embodiments involving an earbud, stress response detection and categorization may also be implemented using one or more other wearables, such as a watch or a phone. One alternative embodiment can estimate the multi-modal biomarkers for stress detection and characterization when the user holds the wrist on which a watch is worn on the chest for a certain period of time. This is an actively-initiated assessment, as compared to the passive assessment using an earbud. However, this assessment could also be passive when someone is lying down on a bed during or after experiencing the stressful event. The watch IMU sensor can capture the mechanical force of pumping the blood by user heart, and the watch PPG can capture the blood flow on the wrist at the same time. Moreover, the watch IMU can also capture the breathing biomarkers (e.g., breathing rate) since the breathing motion is slower frequency compared to the heart motion. Hence, the watch can estimate the heart rate, heart rate variability biomarkers, breathing biomarkers, and hemodynamic biomarkers, which are described above in connection with use of earbuds.

Similar to watch, the phone IMU can also capture the heart motion and breathing motion when the phone is placed on the chest or placed beside the user in the bed when the user is lying down. Several smartphones (e.g., Samsung Galaxy S9) have the ability to concurrently sense PPG if the user's finger is placed on the sensor. One embodiment can utilize the IMU and PPG on the phone to extract the same set of biomarkers described above in connection with use of earbuds. Another embodiment can utilize the combination of the watch and the phone to extract higher quality biomarkers, to determine healthy and unhealthy stress response with greater confidence.

Figure 24:
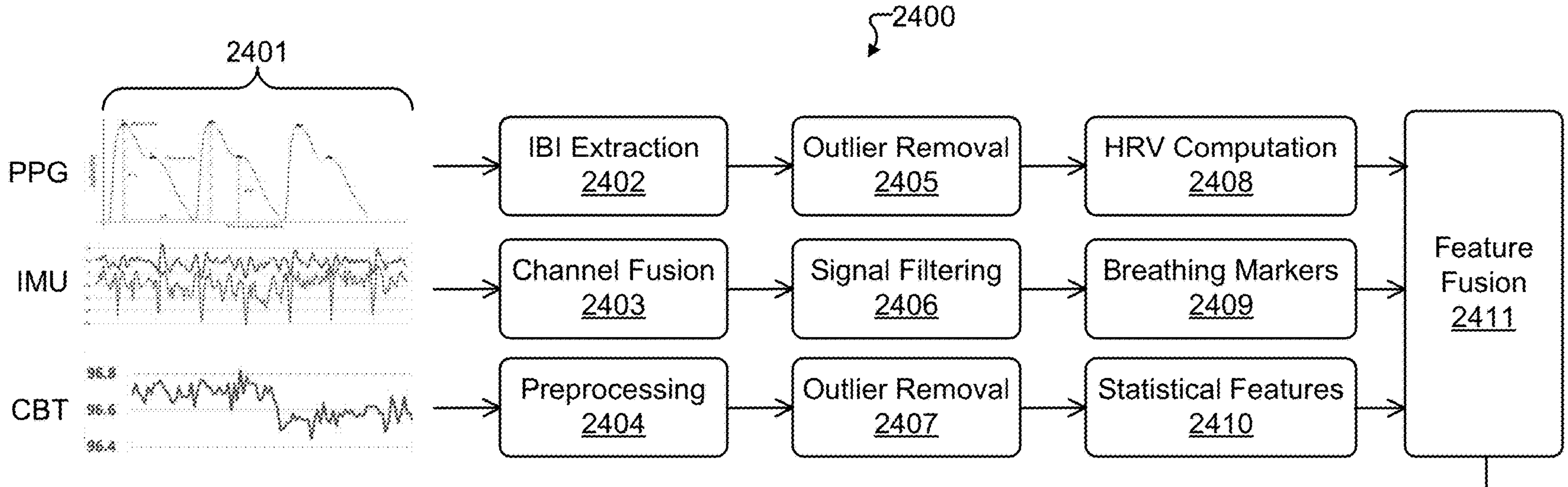
FIG. 24 illustrates an alternative process flow for continuous stress detection using multi-modal biosensing in accordance with this disclosure.
Figure 24:
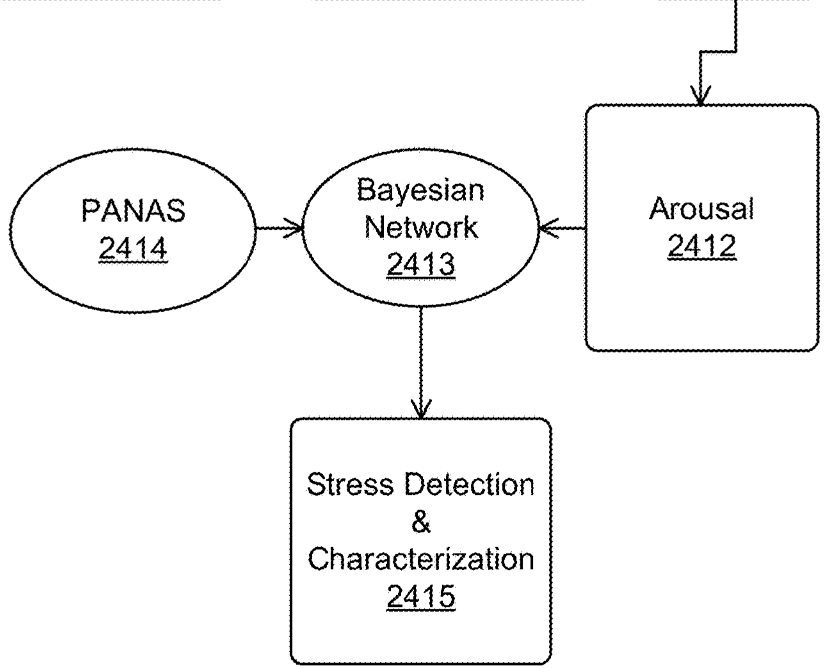

FIG. 24 illustrates an alternative process flow 2400 for continuous stress detection using multi-modal biosensing in accordance with this disclosure. For ease of explanation, the process flow 2400 shown in FIG. 24 is described as being implemented on or supported by one or more components in the network configuration 100 of FIG. 1, such as the electronic device 101, the server 106, or both, and one or more of first and second external electronic devices 102 and 104. However, the process flow 2400 shown in FIG. 24 could be used with any other suitable device(s) and in any other suitable system(s).

An alternative embodiment can also consider self-reported stress outcomes to improve the accuracy of the stress detection model using a Bayesian Network. Process flow 2400 receives multi-modal physiological bio-sensing signals 2401, including PPG, IMU and core body temperature (CBT). The PPG signals are processed by IBI extraction 2402, the IMU signals are processed by channel fusion 2403, and the CBT signals are process by preprocessing 2404. Outlier removal 2405 is performed on the output of IBI extraction 2402, signal filtering 2406 is performed on the output of channel fusion 2403, and outlier removal is performed on the output of preprocessing 2404. IBI extraction 2402, via outlier removal 2405, supplies HRV computation 2408. Channel fusion 2403, via signal filtering 2406, supplies determination of breathing markers 2409. Preprocessing 2404, via outlier removal 2407, supplies determination of statistical features 2410. The outputs of HRV computation 2408, breathing markers determination 2409, and statistical features determination 2410 are collated through feature fusion 2411. The collated features are employed by arousal detection 2412. The significant arousal events from arousal detection 2412 are received, together with positive or negative affect schedule (PANAS) user input 2414, by Bayesian network 2413, which detects and characterizes stress 2415.

Figure 25:
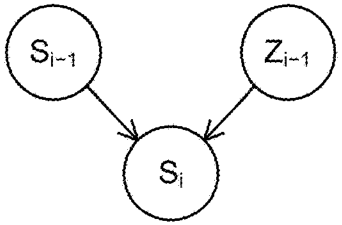
FIG. 25 illustrates a Bayesian network and corresponding conditional probability table for use in the embodiment of FIG. 24 in accordance with this disclosure.

FIG. 25 illustrates, on the left, a Bayesian network that explains the causal relationship between self-reported stress $S_{i-1}$ for minute i−1, the physiological stress arousal $Z_{i-1}$ for minute i−1, and the self-reported stress $S_i$. On the right, FIG. 25 illustrates the corresponding conditional probability table (CPT). The determination of stress within the Bayesian network may be according to:

$$p(S_i=1)=y_i=\alpha y_{i-1}(1-x_{i-1})+\beta(1-y_{i-1})x_{i-1}+y_{i-1}x_{i-1}, \tag{1}$$

$$p(S_i=1)=y_i=\begin{cases}\alpha(1-x_0)+x_0 & \text{if } S_0=1\\ \beta x_0 & \text{otherwise}\end{cases}. \tag{2}$$

Self-report prompts can be associated with the detected arousal segment. However, the self-reported measures still require the user's active participation in the process.

Figure 26:
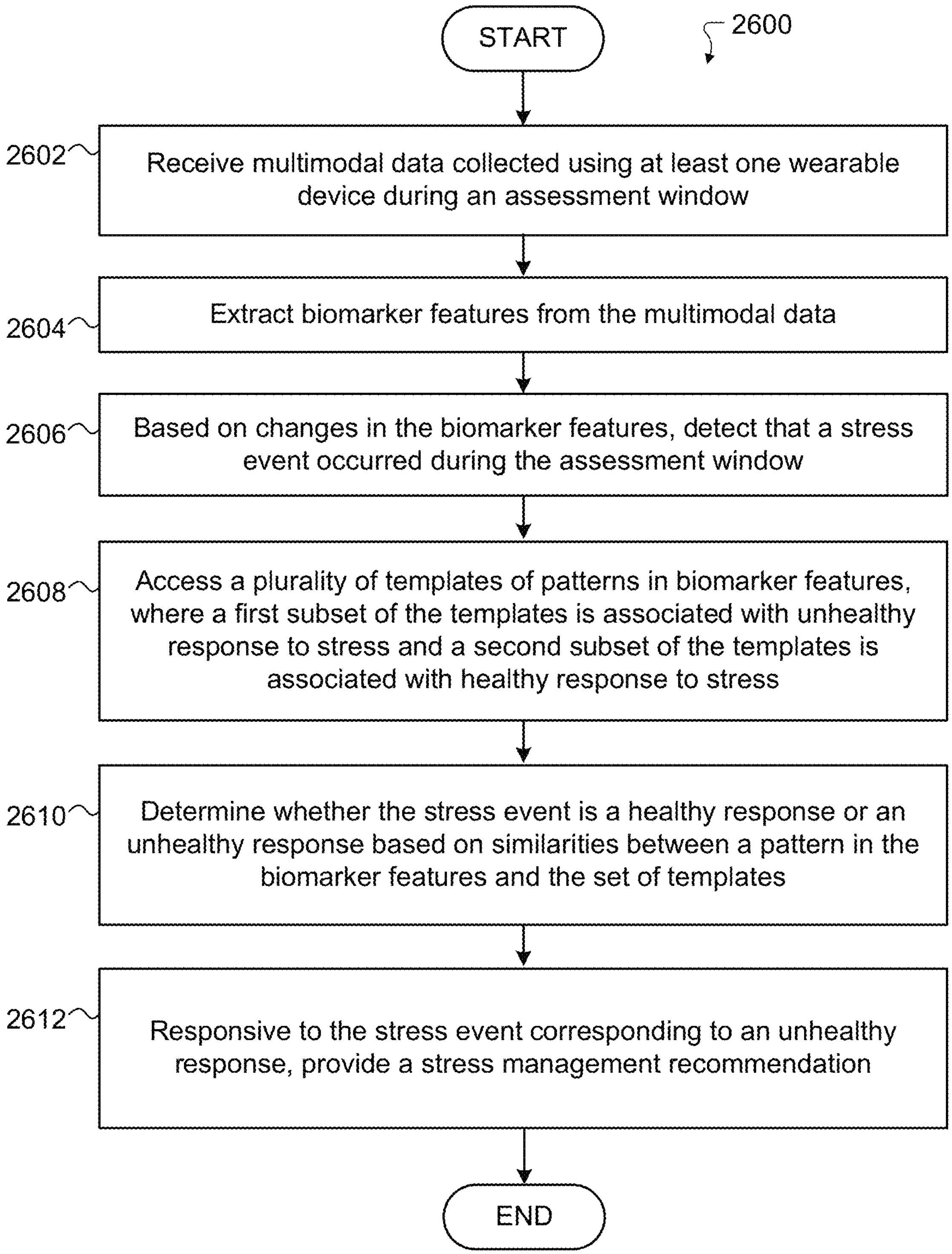
FIG. 26 illustrates an example method for multi-modal stress detection and characterization in accordance with this disclosure.

FIG. 26 illustrates an example method 2600 for multi-modal stress detection and characterization in accordance with this disclosure. For ease of explanation, the method 2600 is described with reference to the process flow 300 and the earbuds including the sensing portions 200. However, the method 2600 may be employed with any suitable process flow and system and may be readily modified to accommodate variations in the underlying process flow and/or system.

As shown in FIG. 26, multimodal data collected using at least one wearable device during an assessment window is received (step 2602). Biomarker features are extracted from the multimodal data (step 2604), and based on changes in the extracted biomarker features, occurrence of a stress event during the assessment window is detected (step 2606). A plurality of templates of patterns in biomarker features, including a first subset of the templates is associated with unhealthy response to stress and a second subset of the templates is associated with healthy response to stress, is accessed (step 2608). Whether the stress event corresponds to a healthy response or an unhealthy response is determined based on similarities between a pattern in the extracted biomarker features and the plurality of templates (step 2610). When the stress event is determined to correspond to an unhealthy response, a stress management recommendation is provided (step 2612).

Although FIG. 26 illustrates one example of a method 2600 for multi-modal stress detection and characterization, various changes may be made to FIG. 26. For example, while shown as a series of steps, various steps in FIG. 26 may overlap, occur in parallel, occur in a different order, or occur any number of times.

Figure 27:
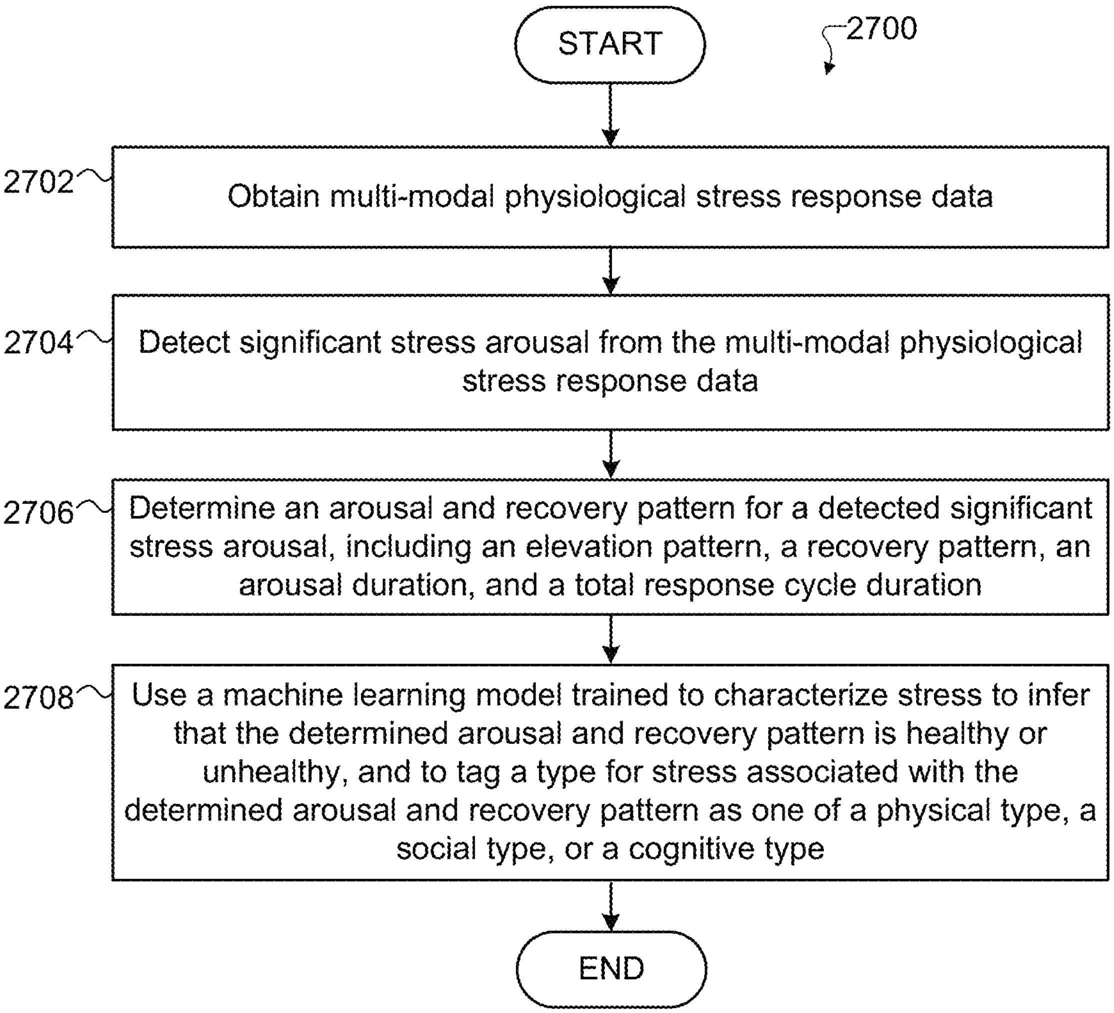
FIG. 27 illustrates an example method for employing an machine learning model in multi-modal stress detection and characterization in accordance with this disclosure.

FIG. 27 illustrates an example method 2700 for employing an ML model in multi-modal stress detection and characterization in accordance with this disclosure. For ease of explanation, the method 2700 is described with reference to the process flow 300 and the earbuds including the sensing portions 200. However, the method 2700 may be employed with any suitable process flow and system and may be readily modified to accommodate variations in the underlying process flow and/or system.

As shown in FIG. 27, multi-modal physiological stress response data is obtained (step 2702). Significant stress arousal, if present, is detected from the multi-modal physiological stress response data (step 2704). An arousal and recovery pattern for a detected significant stress arousal is determined (step 2706). The arousal and recovery pattern includes an elevation pattern, a recovery pattern, an arousal duration, and a total response cycle duration. A machine learning model, trained to characterize stress based on selected multi-modal biomarker features, is used to infer that the determined arousal and recovery pattern is healthy or unhealthy, and to tag a type for stress associated with the determined arousal and recovery pattern as one of a physical type, a social type, or a cognitive type (step 2708).

Although FIG. 27 illustrates one example of a method 2700 for employing an ML model in multi-modal stress detection and characterization, various changes may be made to FIG. 27. For example, while shown as a series of steps, various steps in FIG. 27 may overlap, occur in parallel, occur in a different order, or occur any number of times.

The various embodiments disclosed herein may be utilized for stress management for mental health improvement, with (for example) depression, anxiety, and/or sleep disorder (s). The embodiments may implement passive intervention, such as haptic feedback to a watch prompting (for example) breathing exercises (e.g., 4-7-8 breathing). The embodiments may also be utilized for personalized music recommendations, for better focus and productivity.

Although this disclosure has been described with reference to various example embodiments, various changes and modifications may be suggested to one skilled in the art. It is intended that this disclosure encompass such changes and modifications as fall within the scope of the appended claims.

What is claimed is:

1. A method comprising:

collecting physiological data from earbuds including at least one photoplethysmography (PPG) sensor and at least one inertial measurement unit (IMU) during an assessment window;

receiving multimodal data collected using the earbuds during the assessment window;

extracting biomarker features from the multimodal data, the extracted biomarker features corresponding to at least lung motion, motion due to heart pumping, and body appendage motion;

based on changes in the extracted biomarker features, detecting that a stress event occurred during the assessment window;

accessing a plurality of templates of patterns in biomarker features, wherein a first subset of the templates is associated with unhealthy response to stress and a second subset of the templates is associated with healthy response to stress;

determining whether the stress event corresponds to a healthy response or an unhealthy response based on similarities between a pattern in the extracted biomarker features and the plurality of templates; and responsive to the stress event corresponding to an unhealthy response, providing a stress management recommendation tailored based on the detected stress event and personalized to an individual wearing the earbuds and associated with at least one other device communicably coupled to the earbuds, the stress management recommendation displayed on the at least one other device, and initiating a stress management intervention at one or more of the earbuds and the at least one other device based on the stress management recommendation, the stress management intervention comprising one or more of a haptic reminder, an auditory cue, or music.

2. The method of claim 1, wherein the multimodal data includes PPG data and IMU data, and one or more of electrocardiogram data and body temperature data.

3. The method of claim 1, wherein the at least one other device is one of a watch or a phone.

4. The method of claim 1, wherein the extracted biomarker features include one or more of: a heart rate, a time domain heart rate variability, a frequency domain heart rate variability, a non-linear heart rate variability, a breathing rate, an inhalation to exhalation ratio, a depth of breathing, a cardiac output, a stroke volume, a pulse transit time, or a pre-ejection period.

5. The method of claim 1, wherein the templates are associated with one or more of an anticipatory reaction, a lack of recovery, a lack of habituation, and repeated exposure.

6. The method of claim 1, wherein determining whether the stress event is a healthy response or an unhealthy response further comprises:

for each one of the plurality of templates, determining a similarity score between the pattern in the extracted biomarker features and a respective one of the plurality of templates; and providing similarity scores and one or more response features associated with the extracted biomarker features as input to a machine learning model, the machine learning model trained to predict whether the stress event is a healthy response or an unhealthy response based on a probability distribution.

7. The method of claim 6, wherein the one or more response features include one or more of a level of changes from a baseline, elevation patterns, recovery patterns, an elevation duration, and a total stress event duration.

8. An apparatus comprising:

at least one processing device configured to:

collect physiological data from earbuds including at least one photoplethysmography (PPG) sensor and at least one inertial measurement unit (IMU) during an assessment window;

receive multimodal data collected using the earbuds during the assessment window;

extract biomarker features from the multimodal data, the extracted biomarker features corresponding to at least lung motion, motion due to heart pumping, and body appendage motion;

based on changes in the extracted biomarker features, detect that a stress event occurred during the assessment window;

access a plurality of templates of patterns in biomarker features, wherein a first subset of the templates is associated with unhealthy response to stress and a second subset of the templates is associated with healthy response to stress;

determine whether the stress event corresponds to a healthy response or an unhealthy response based on similarities between a pattern in the extracted biomarker features and the plurality of templates; and responsive to the stress event corresponding to an unhealthy response, provide a stress management recommendation tailored based on the detected stress event and personalized to an individual wearing the earbuds and associated with at least one other device communicably coupled to the earbuds, the stress management recommendation displayed on the at least one other device, and initiate a stress management intervention at one or more of the earbuds and the at least one other device based on the stress management recommendation, the stress management intervention comprising one or more of a haptic reminder, an auditory cue, or music.

9. The apparatus of claim 8, wherein the multimodal data includes PPG data and IMU data, and one or more of electrocardiogram data and body temperature data.

10. The apparatus of claim 8, wherein the at least one other device is one of a watch or a phone.

11. The apparatus of claim 8, wherein the extracted biomarker features include one or more of: a heart rate, a time domain heart rate variability, a frequency domain heart rate variability, a non-linear heart rate variability, a breathing rate, an inhalation to exhalation ratio, a depth of breathing, a cardiac output, a stroke volume, a pulse transit time, or a pre-ejection period.

12. The apparatus of claim 8, wherein the templates are associated with one or more of an anticipatory reaction, a lack of recovery, a lack of habituation, and repeated exposure.

13. The apparatus of claim 8, wherein, to determine whether the stress event is a healthy response or an unhealthy response, the at least one processing device is further configured to:

for each one of the plurality of templates, determine a similarity score between the pattern in the extracted biomarker features and a respective one of the plurality of templates; and provide similarity scores and one or more response features associated with the extracted biomarker features as input to a machine learning model, the machine learning model trained to predict whether the stress event is a healthy response or an unhealthy response based on a probability distribution.

14. The apparatus of claim 13, wherein the one or more response features include one or more of a level of changes from a baseline, elevation patterns, recovery patterns, an elevation duration, and a total stress event duration.

15. A non-transitory computer readable medium containing instructions that when executed cause at least one processor of an electronic device to:

collect physiological data from earbuds including at least one photoplethysmography (PPG) sensor and at least one inertial measurement unit (IMU) during an assessment window;

receive multimodal data collected using the earbuds during the assessment window;

extract biomarker features from the multimodal data, the extracted biomarker features corresponding to at least lung motion, motion due to heart pumping, and body appendage motion;

based on changes in the extracted biomarker features, detect that a stress event occurred during the assessment window;

access a plurality of templates of patterns in biomarker features, wherein a first subset of the templates is associated with unhealthy response to stress and a second subset of the templates is associated with healthy response to stress;

determine whether the stress event corresponds to a healthy response or an unhealthy response based on similarities between a pattern in the extracted biomarker features and the plurality of templates; and responsive to the stress event corresponding to an unhealthy response, provide a stress management recommendation tailored based on the detected stress event and personalized to an individual wearing the earbuds and associated with at least one other device communicably coupled to the earbuds, the stress management recommendation displayed on the at least one other device, and initiate a stress management intervention at one or more of the earbuds and the at least one other device based on the stress management recommendation, the stress management intervention comprising one or more of a haptic reminder, an auditory cue, or music.

16. The non-transitory computer readable medium of claim 15, wherein the multimodal data includes PPG data and IMU data, and one or more of electrocardiogram data and body temperature data.

17. The non-transitory computer readable medium of claim 15, wherein the at least one other device is one of a watch or a phone.

18. The non-transitory computer readable medium of claim 15, wherein the extracted biomarker features include one or more of: a heart rate, a time domain heart rate variability, a frequency domain heart rate variability, a non-linear heart rate variability, a breathing rate, an inhalation to exhalation ratio, a depth of breathing, a cardiac output, a stroke volume, a pulse transit time, or a pre-ejection period.

19. The non-transitory computer readable medium of claim 15, wherein the templates are associated with one or more of an anticipatory reaction, a lack of recovery, a lack of habituation, and repeated exposure.

20. The non-transitory computer readable medium of claim 15, wherein the instructions when executed cause the at least one processor to determine whether the stress event is a healthy response or an unhealthy response comprise instructions that when executed cause the at least one processor to:

for each one of the plurality of templates, determine a similarity score between the pattern in the extracted biomarker features and a respective one of the plurality of templates; and provide similarity scores and one or more response features associated with the extracted biomarker features as input to a machine learning model, the machine learning model trained to predict whether the stress event is a healthy response or an unhealthy response based on a probability distribution.

* * * * *